(12) United States Patent
Staheli et al.

(10) Patent No.: US 12,128,371 B2
(45) Date of Patent: *Oct. 29, 2024

(54) FLUID MIXING SYSTEM WITH FLEXIBLE DRIVE LINE AND FOLDABLE IMPELLER

(71) Applicant: LIFE TECHNOLOGIES CORPORATION, Carlsbad, CA (US)

(72) Inventors: Clinton C. Staheli, Brigham City, UT (US); Brandon M. Knudsen, Hyrum, UT (US); Trevor G. Williams, Providence, UT (US); Steven R. Kjar, Logan, UT (US)

(73) Assignee: LIFE TECHNOLOGIES CORPORATION, Carslbad, CA (US)

( * ) Notice: Subject to any disclaimer, the term of this patent is extended or adjusted under 35 U.S.C. 154(b) by 880 days.

This patent is subject to a terminal disclaimer.

(21) Appl. No.: 16/358,263

(22) Filed: Mar. 19, 2019

(65) Prior Publication Data

US 2019/0209981 A1 Jul. 11, 2019

Related U.S. Application Data

(63) Continuation of application No. 15/803,327, filed on Nov. 3, 2017, now Pat. No. 10,272,400, which is a
(Continued)

(51) Int. Cl.
*B01F 27/054* (2022.01)
*B01F 27/07* (2022.01)
(Continued)

(52) U.S. Cl.
CPC ........ *B01F 27/212* (2022.01); *B01F 27/0541* (2022.01); *B01F 27/071* (2022.01);
(Continued)

(58) Field of Classification Search
CPC .............. B01F 7/00058; B01F 7/00066; B01F 7/00075; B01F 27/0541; B01F 27/0542; B01F 27/0543; C12M 23/14; C12M 27/02
(Continued)

(56) References Cited

U.S. PATENT DOCUMENTS 94,614 A * 9/1869 Lamey ..................... F03B 3/00
416/143
659,345 A 10/1900 Ivins
(Continued)

FOREIGN PATENT DOCUMENTS

CN 101058062 A 10/2007
CN 101163538 A 4/2008
(Continued)

OTHER PUBLICATIONS

European Search Report dated Feb. 3, 2020, issued in EP Application No. 19193563.4.
(Continued)

*Primary Examiner* — David L Sorkin

(57) ABSTRACT

A fluid mixing system includes a container, such as a flexible bag, bounding a compartment. A flexible drive line is disposed within the compartment, the drive line having a first end rotatably connected to a first end of the container and an opposing second end rotatably connected to a second end of the container. At least one mixing element, such as an impeller, can be coupled with the flexible drive line. Rotation of the drive line facilitates rotation of the impeller within the container.

26 Claims, 31 Drawing Sheets

Related U.S. Application Data continuation of application No. 14/390,956, filed as application No. PCT/US2013/031608 on Mar. 14, 2013, now Pat. No. 9,839,886.

(60) Provisional application No. 61/621,064, filed on Apr. 6, 2012.

(51) Int. Cl.

| | | |
|---|---|---|
| *B01F 27/072* | (2022.01) | |
| *B01F 27/1125* | (2022.01) | |
| *B01F 27/191* | (2022.01) | |
| *B01F 27/21* | (2022.01) | |
| *B01F 27/2111* | (2022.01) | |
| *B01F 27/88* | (2022.01) | |
| *B01F 27/906* | (2022.01) | |
| *B01F 35/41* | (2022.01) | |
| *B01F 35/513* | (2022.01) | |
| *C12M 1/00* | (2006.01) | |
| *C12M 1/06* | (2006.01) | |

(52) U.S. Cl.
CPC ...... *B01F 27/0726* (2022.01); *B01F 27/1125* (2022.01); *B01F 27/11253* (2022.01); *B01F 27/191* (2022.01); *B01F 27/2111* (2022.01); *B01F 27/88* (2022.01); *B01F 27/906* (2022.01); *B01F 35/41* (2022.01); *B01F 35/4111* (2022.01); *B01F 35/4121* (2022.01); *B01F 35/513* (2022.01); *C12M 23/14* (2013.01); *C12M 23/52* (2013.01); *C12M 27/02* (2013.01)

(58) Field of Classification Search
USPC .................................................. 366/280, 308
See application file for complete search history.

(56) References Cited

U.S. PATENT DOCUMENTS

| | | | |
|---|---|---|---|
| 1,227,671 A * | 5/1917 | Robertson | B64C 11/343 416/131 |
| 1,436,172 A * | 11/1922 | Holmgren | B01F 7/00066 366/251 |
| 1,711,114 A | 4/1929 | Hunt | |
| 1,752,833 A | 4/1930 | Brumder | |
| 1,778,188 A | 10/1930 | Guy | |
| 1,898,724 A | 2/1933 | Gifford | |
| 1,954,093 A | 4/1934 | Nelson | |
| 2,552,057 A | 5/1951 | Paik | |
| 2,896,926 A | 7/1959 | Chapman | |
| 3,281,124 A | 10/1966 | Bartl | |
| 3,322,401 A | 5/1967 | Mersch | |
| 3,455,540 A * | 7/1969 | Marcmann | B01F 7/00066 416/142 |
| 3,559,962 A | 2/1971 | Enssle et al. | |
| 3,692,427 A | 9/1972 | Risse | |
| 4,083,653 A | 4/1978 | Stiffler | |
| 4,355,906 A | 10/1982 | Ono | |
| D273,709 S | 5/1984 | Schneider | |
| 4,712,922 A | 12/1987 | Feterl | |
| 4,722,608 A | 2/1988 | Salzman et al. | |
| D336,034 S | 6/1993 | Rebilas | |
| 5,411,331 A | 5/1995 | Griffin | |
| 5,454,797 A | 10/1995 | Haswell | |
| D373,709 S | 9/1996 | Leu | |
| 5,885,001 A | 3/1999 | Thomas | |
| 5,896,989 A | 4/1999 | Ropiak et al. | |
| 5,941,636 A | 8/1999 | Lu | |
| 5,972,695 A | 10/1999 | Murofushi et al. | |
| 6,083,587 A | 7/2000 | Smith et al. | |
| D439,328 S | 3/2001 | Nielsen | |
| 6,655,655 B1 | 12/2003 | Matkovich et al. | |
| 6,670,171 B2 | 12/2003 | Carli | |
| 6,844,186 B2 | 1/2005 | Carli | |
| 6,884,186 B2 | 4/2005 | Fluckiger et al. | |
| 6,884,786 B1 | 4/2005 | Kieny et al. | |
| 7,229,206 B2 | 6/2007 | Whitney | |
| 7,384,783 B2 | 6/2008 | Kunas et al. | |
| 7,441,940 B2 | 10/2008 | Vanek | |
| 7,487,688 B2 | 2/2009 | Goodwin | |
| 7,682,067 B2 | 3/2010 | West et al. | |
| 7,878,099 B2 | 2/2011 | Loibl | |
| 7,879,599 B2 | 2/2011 | Goodwin et al. | |
| D662,212 S | 6/2012 | Quisenberry | |
| 8,272,410 B2 | 9/2012 | Elgan et al. | |
| 8,292,491 B2 | 10/2012 | Castillo et al. | |
| 8,342,737 B2 | 1/2013 | Greller et al. | |
| 8,348,737 B2 | 1/2013 | Page | |
| D679,023 S | 3/2013 | Quisenberry | |
| 8,439,554 B2 | 5/2013 | Kaas | |
| 8,455,242 B2 | 6/2013 | Staheli et al. | |
| 8,506,198 B2 | 8/2013 | West et al. | |
| 8,603,805 B2 | 12/2013 | Goodwin et al. | |
| 8,641,314 B2 | 2/2014 | Thacker et al. | |
| 9,005,971 B2 | 4/2015 | Goodwin et al. | |
| 9,388,375 B2 | 7/2016 | Brau et al. | |
| 9,392,553 B2 | 7/2016 | Haim et al. | |
| 9,643,133 B2 | 5/2017 | Goodwin et al. | |
| 9,839,886 B2 | 12/2017 | Staheli | |
| 9,932,553 B2 | 4/2018 | Brau et al. | |
| D824,042 S | 7/2018 | Scott et al. | |
| D830,544 S | 10/2018 | Kisner et al. | |
| 10,272,400 B2 * | 4/2019 | Staheli | B01F 7/00683 |
| D857,188 S | 8/2019 | Moran et al. | |
| D870,315 S | 12/2019 | Wahlqvist et al. | |
| D870,989 S | 12/2019 | Penland | |
| 2002/0105856 A1 | 8/2002 | Terentiev | |
| 2002/0131654 A1 | 9/2002 | Smith et al. | |
| 2003/0008389 A1 * | 1/2003 | Carll | B01F 11/04 435/302.1 |
| 2003/0077466 A1 | 4/2003 | Smith et al. | |
| 2006/0196501 A1 | 9/2006 | Bibbo et al. | |
| 2006/0240546 A1 | 10/2006 | Goodwin et al. | |
| 2006/0270036 A1 | 11/2006 | Goodwin et al. | |
| 2006/0280028 A1 * | 12/2006 | West | B01F 7/00691 366/331 |
| 2007/0014187 A1 | 1/2007 | Kaas | |
| 2008/0032389 A1 | 2/2008 | Selker et al. | |
| 2008/0116012 A1 | 5/2008 | Ferguson | |
| 2008/0151686 A1 * | 6/2008 | Meadows | B01F 15/00883 366/274 |
| 2010/0014379 A1 | 1/2010 | Wright et al. | |
| 2010/0149908 A1 | 6/2010 | Singh et al. | |
| 2010/0165785 A1 | 7/2010 | Kaas | |
| 2010/0260010 A1 | 10/2010 | Jornitz | |
| 2011/0013473 A1 | 1/2011 | Ludwig et al. | |
| 2011/0013474 A1 | 1/2011 | Ludwig et al. | |
| 2011/0026360 A1 | 2/2011 | Greller et al. | |
| 2011/0058447 A1 | 3/2011 | Reif et al. | |
| 2011/0058448 A1 | 3/2011 | Reif et al. | |
| 2011/0188928 A1 | 8/2011 | West et al. | |
| 2011/0207218 A1 | 8/2011 | Staheli et al. | |
| 2011/0229963 A1 | 9/2011 | Fatherazi et al. | |
| 2011/0310696 A1 | 12/2011 | Goodwin et al. | |
| 2011/0312087 A1 | 12/2011 | Khan | |
| 2013/0082410 A1 | 4/2013 | Goodwin et al. | |
| 2013/0101982 A1 | 4/2013 | Goodwin et al. | |
| 2013/0279289 A1 | 10/2013 | Eggler et al. | |
| 2013/0288346 A1 | 10/2013 | Tuohey et al. | |
| 2014/0106453 A1 | 4/2014 | Kunas et al. | |
| 2015/0011714 A1 | 1/2015 | Ichihara et al. | |
| 2015/0117142 A1 | 4/2015 | Staheli et al. | |
| 2015/0118753 A1 | 4/2015 | Brau et al. | |
| 2017/0011714 A1 | 1/2017 | Eim et al. | |
| 2017/0183617 A1 | 6/2017 | Jones et al. | |

FOREIGN PATENT DOCUMENTS

| | | |
|---|---|---|
| CN | 102112595 A | 6/2011 |
| CN | 102729330 A | 10/2012 |
| CN | 102803463 A | 11/2012 |

(56) References Cited

FOREIGN PATENT DOCUMENTS

| | | |
|---|---|---|
| CN | 202606066 U | 12/2012 |
| CN | 104619827 A | 5/2015 |
| DE | 202009005407 U1 | 9/2009 |
| DE | 102008058338 A1 | 5/2010 |
| EP | 1 776 998 A1 | 4/2007 |
| EP | 2123745 A2 | 11/2009 |
| FR | 782935 | 9/1934 |
| JP | H06285353 A | 10/1994 |
| JP | H08-224093 A | 9/1996 |
| JP | 2002-234023 A | 8/2002 |
| JP | 2004-524103 A | 8/2004 |
| JP | 2004-532719 A | 10/2004 |
| JP | 2009-513140 A | 4/2009 |
| JP | 2013-544186 A | 12/2013 |
| WO | 2010/089151 A1 | 8/2010 |
| WO | 2011/139209 A1 | 11/2011 |
| WO | 2012/097079 A2 | 7/2012 |
| WO | 2013/151733 A1 | 10/2013 |
| WO | WO-2014/172047 A1 | 10/2014 |
| WO | 2015/039034 A1 | 3/2015 |
| WO | 2017/023638 A1 | 2/2017 |
| WO | 2017/064058 A1 | 4/2017 |

OTHER PUBLICATIONS

Partial International Search Report dated Jun. 12, 2013, issued in PCT Application No. PCT/US2013/031608, filed Mar. 14, 2013.
International Search Report and Written Opinion dated Aug. 6, 2013, issued in PCT Application No. PCT/US2013/031608, filed Mar. 14, 2013.
ATMI Life Sciences, *Integrity PadReactor, A New Culture in Cell Growth*, published as early as 2010, 4 pages.
ATMI Life Sciences, *Integrity PadReactor, All Applications, High-End Controls and Abilities*, published as early as 2010, 4 pages.
EP19193563.4, Extended Search Report, dated Jun. 3, 2020, 13 pages.
EP19193563.4, Partial Search Report, dated Feb. 3, 2020, 12 pages.
De Wilde, Davy, et al. "Superior scalability of single-use bioreactors." Innovations in Cell Culture 14 (2014): 14-19. (Year: 2014).
Stoker, Emily B., "Comparative Studies on Scale-Up Methods of Single-Use Bioreactors" (2011). All Graduate Theses and Dissertations. 889. (Year: 2011).
Xing, Z., et al.. (2009). Scale-up analysis for a CHO cell culture process in large-scale bioreactors. In Biotechnology and Bioengineering (vol. 103, Issue 4, pp. 733-746). Wiley. (Year: 2009).
Yang, J.- D et al. (2007). Fed-batch bioreactor process scale-up from 3-L to 2,500-L scale for monoclonal antibody production from cell culture. In Biotechnology and Bioengineering (vol. 98, Issue 1, pp. 141-154). Wiley. (Year: 2007).

\* cited by examiner

FLUID MIXING SYSTEM WITH FLEXIBLE DRIVE LINE AND FOLDABLE IMPELLER

CROSS-REFERENCE TO RELATED APPLICATIONS

This application is a continuation of U.S. application Ser. No. 15/803,327, filed Nov. 3, 2017, which is a continuation of U.S. application Ser. No. 14/390,956, filed Oct. 6, 2014, now U.S. Pat. No. 9,839,886, issued Dec. 12, 2017, which is a nationalization of PCT Application No. PCT/US2013/031608, filed Mar. 14, 2013, which claims the benefit of U.S. Provisional Application No. 61/621,064, filed on Apr. 6, 2012, which are incorporated herein by reference.

BACKGROUND OF THE INVENTION

1. The Field of the Invention

The present invention relates to fluid mixing systems and, more specifically, fluid mixing systems having a flexible drive line and/or an impeller having pivotable blades.

2. The Relevant Technology

The biopharmaceutical industry uses a broad range of mixing systems for a variety of processes such as in the preparation of media and buffers and in the growing, mixing and suspension of cells and microorganisms. Some conventional mixing systems, including bioreactors and fermentors, comprise a flexible bag disposed within a rigid support housing. An impeller is disposed within the flexible bag and is coupled with the drive shaft. Rotation of the drive shaft and impeller facilitates mixing and/or suspension of the fluid contained within the flexible bag.

Although the current mixing systems are useful, they have some limitations. For example, where the drive shaft is secured within the flexible bag during the manufacturing process, the rigid drive shaft limits the ability to collapse or fold the flexible bag so as to reduce its size for transportation, storage and/or further processing. Likewise, where it is intended to reuse the drive shaft, such as when it is made of metal, this system has the disadvantage of needing to clean and sterilize the drive shaft between different uses.

In an alternative conventional system, a rotatable tube extends into the flexible bag and has an impeller coupled at the end thereof. During use, the rigid drive shaft is passed down into the tube and couples with the impeller. In turn, rotation of the drive shaft facilitates rotation of the impeller for mixing the fluid within the flexible bag. In this design, with the drive shaft removed, the flexible bag with tube can be folded for ease of storage and transportation. In addition, because the drive shaft does not directly contact the fluid within the bag, the drive shaft does not need to be cleaned or sterilized between uses.

However, the flexible bag is typically secured within the support housing prior to insertion of the drive shaft. It is thus necessary during use to vertically position the drive shaft over the top of the bag for insertion into the tube. For large bags or elongated bags that require a long drive shaft, this can be difficult to accomplish. Furthermore, in situations where the mixing system is located in a room with a relatively low ceiling, it may be impossible to vertically lift the drive shaft over the bag. This type of system also requires increased training in user operation to ensure that the drive shaft is properly received within the tube and properly engaged with the impeller so that the system operates as intended.

Conventional systems also have the drawback that the rigid impellers located within the bags limit the extent to which the bags can be collapsed by folding or other manipulation. Likewise, there are potential concerns that the blades of the impellers can puncture or otherwise damage the bags when the bags are folded around the impeller. In addition, folding the bag around the impeller can place unwanted stress on the rigid impeller blades.

Accordingly, what is needed in the art are mixing systems that solve all or some of the above problems.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

As used in the specification and appended claims, directional terms, such as "top," "bottom," "left," "right," "up," "down," "upper," "lower," "proximal," "distal" and the like are used herein solely to indicate relative directions and are not otherwise intended to limit the scope of the invention or claims.

The present invention relates to systems and methods for mixing fluids such as solutions or suspensions. The systems can be commonly used as bioreactors or fermentors for culturing cells or microorganisms. By way of example and not by limitation, the inventive systems can be used in culturing bacteria, fungi, algae, plant cells, animal cells, protozoan, nematodes, and the like. The systems can accommodate cells and microorganisms that are aerobic or anaerobic and are adherent or non-adherent. The systems can also be used in association with the formation and/or treatment of solutions and/or suspensions that are for biological purposes, such as media, buffers, or reagents. For example, the systems can be used in the formation of media where sparging is used to control the pH of the media through adjustment of the carbonate/bicarbonate levels with controlled gaseous levels of carbon dioxide. The systems can also be used for mixing powders or other components into a liquid where sparging is not required and/or where the solution/suspension is not for biological purposes.

Figure 1:
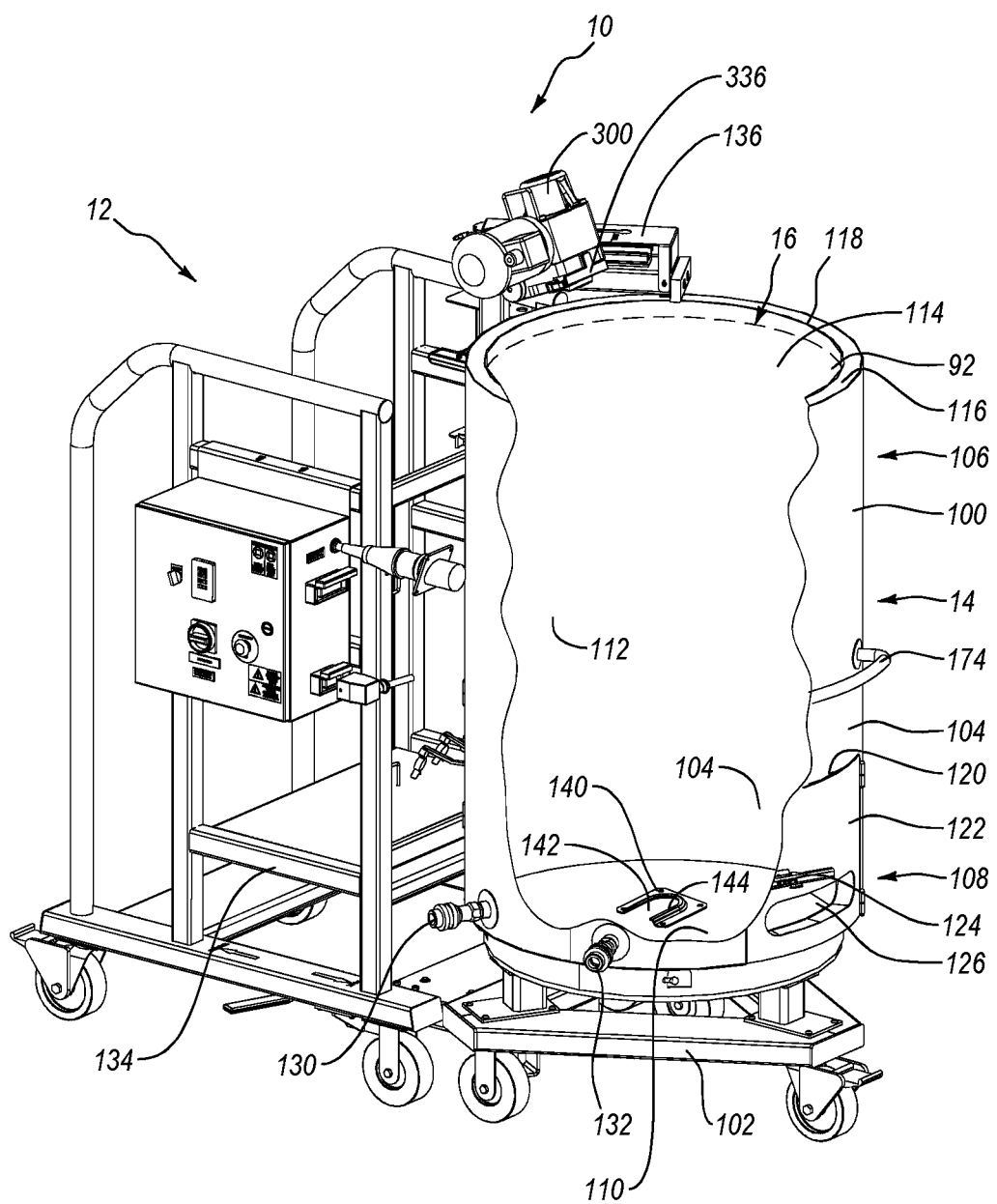
FIG. 1 is a perspective view of a support housing and docking station forming part of a fluid mixing system.
Figure 2:
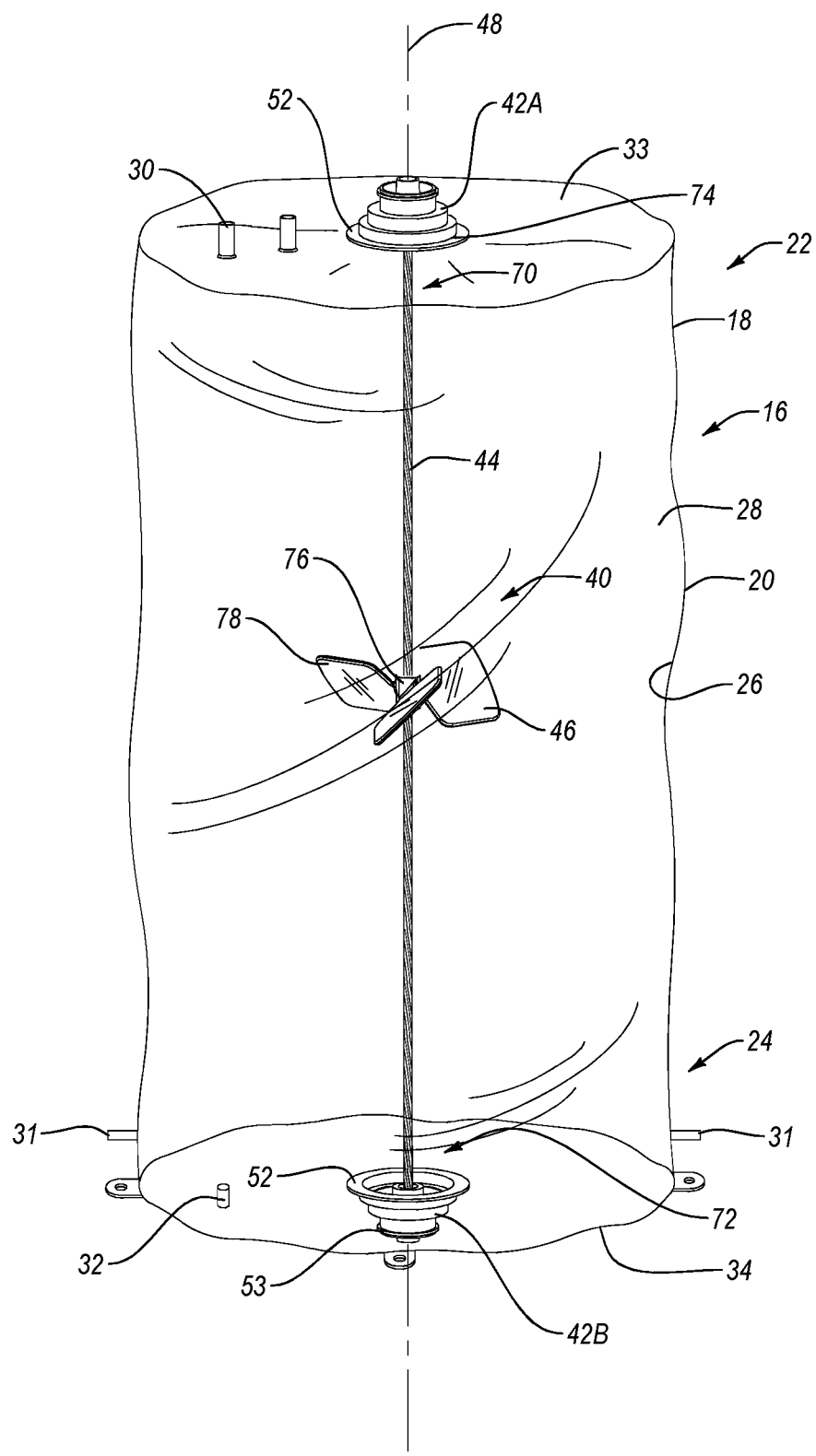
FIG. 2 is a perspective view of a container assembly for use with a support housing shown in FIG. 1.
Figure 3:
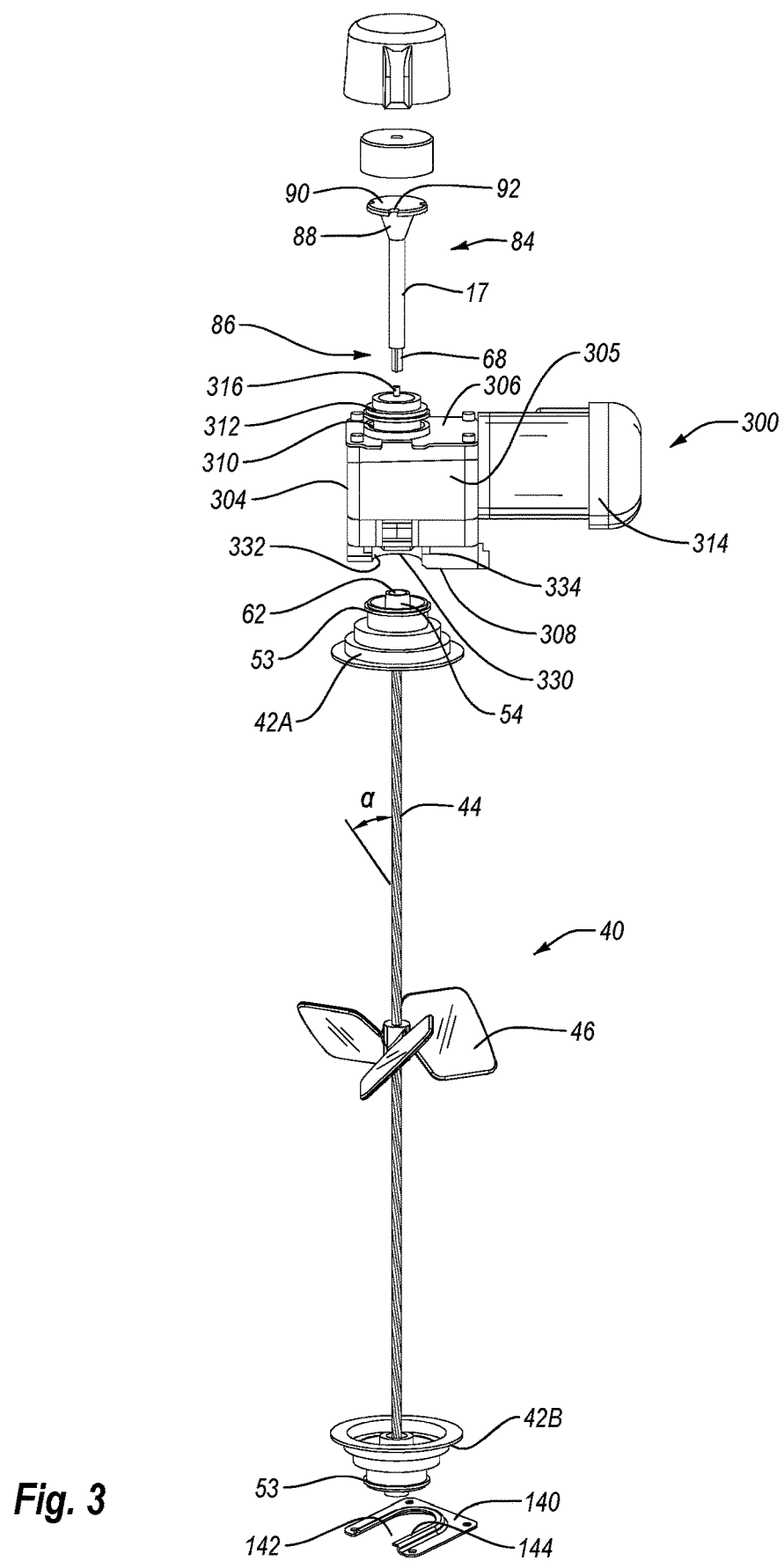
FIG. 3 is a partially exploded view of the impeller assembly, drive motor assembly, and drive shaft of the fluid mixing system.

Depicted in FIGS. 1-3 is one embodiment of an inventive mixing system 10 incorporating features of the present invention. In general, mixing system 10 comprises a docking station 12, a container station 14 that removably docks with docking station 12, a container assembly 16 (FIG. 2) that is supported by container station 14, and a drive shaft 17 (FIG. 3) that extends between docking station 12 and container assembly 16. Container assembly 16 houses the fluid that is mixed. The various components of mixing system 10 will now be discussed in greater detail.

As depicted in FIG. 2, container assembly 16 comprises a container 18 having a side 20 that extends from an upper end 22 to an opposing lower end 24. Upper end 22 terminates at an upper end wall 33 while lower end 24 terminates at a lower end wall 34. Container 18 also has an interior surface 26 that bounds a compartment 28. Compartment 28 is configured to hold a fluid. In the embodiment depicted, container 18 comprises a flexible bag that is comprised of a flexible, water impermeable material such as a low-density polyethylene or other polymeric sheets or film having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive. Examples of extruded material that can be used in the present invention include the HyQ CX3-9 and HyQ CX5-14 films available from HyClone Laboratories, Inc. out of Logan, Utah. The material can be approved for direct contact with living cells and be capable of maintaining a solution sterile. In such an embodiment, the material can also be sterilizable such as by ionizing radiation.

In one embodiment, container 18 can comprise a two-dimensional pillow style bag. In another embodiment, container 18 can be formed from a continuous tubular extrusion of polymeric material that is cut to length. The ends can be seamed closed or panels can be sealed over the open ends to form a three-dimensional bag. Three-dimensional bags not only have an annular side wall but also a two dimensional top end wall and a two dimensional bottom end wall. Three dimensional containers can comprise a plurality of discrete panels, typically three or more, and more commonly four or six. Each panel is substantially identical and comprises a portion of the side wall, top end wall, and bottom end wall of the container. Corresponding perimeter edges of each panel are seamed together. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1, published Sep. 19, 2002 which is incorporated herein by specific reference in its entirety.

It is appreciated that container 18 can be manufactured to have virtually any desired size, shape, and configuration. For example, container 18 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes. The size of the compartment can also be in the range between any two of the above volumes. Although container 18 can be any shape, in one embodiment container 18 is specifically configured to be generally complementary to the chamber on container station 14 in which container 18 is received so that container 18 is properly supported within the chamber.

Although in the above discussed embodiment container 18 is depicted as a flexible bag, in alternative embodiments it is appreciated that container 18 can comprise any form of collapsible container or semi-rigid container. Container 18 can also be transparent or opaque.

Continuing with FIG. 2, formed on container 18 are a plurality of ports 30 at upper end 22, a plurality of ports 31 on opposing sides of side 20 at lower end 24 and a port 32 on lower end wall 34. Each of ports 30-32 communicate with compartment 28. Although only a few ports 30-32 are shown, it is appreciated that container 18 can be formed with any desired number of ports 30-32 and that ports 30-32 can be formed at any desired location on container 18. Ports 30-32 can be the same configuration or different configurations and can be used for a variety of different purposes. For example, ports 30 can be coupled with fluid lines for delivering media, cell cultures, and/or other components into container 18 and withdrawing fluid from container 18. Ports 30 can also be used for delivering gas to container 18, such as through a sparger, and withdrawing gas from container 18.

Ports 30-32 can also be used for coupling probes and/or sensors to container 18. For example, when container 18 is used as a bioreactor or fermentor for growing cells or microorganisms, ports 30-32 can be used for coupling probes such as temperature probes, pH probes, dissolved oxygen probes, and the like. Various optical sensors and other types of sensors can also be attached to ports 30-32. Examples of ports 30-32 and how various probes, sensors, and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference in their entirety. Ports 30-32 can also be used for coupling container 18 to secondary containers, to condenser systems, and to other desired fittings.

Container assembly 16 further comprises an impeller assembly 40. Impeller assembly 40 comprises a first rotational assembly 42A mounted on upper end wall 33, a second rotational assembly 42B mounted on lower end wall 34, a flexible drive line 44 that extends between rotational assemblies 42A and 42B, and an impeller 46 coupled to drive line 44. Drive line 44 has a longitudinal axis 48 that extends along the length thereof and can centrally extend therethrough.

Figure 4:
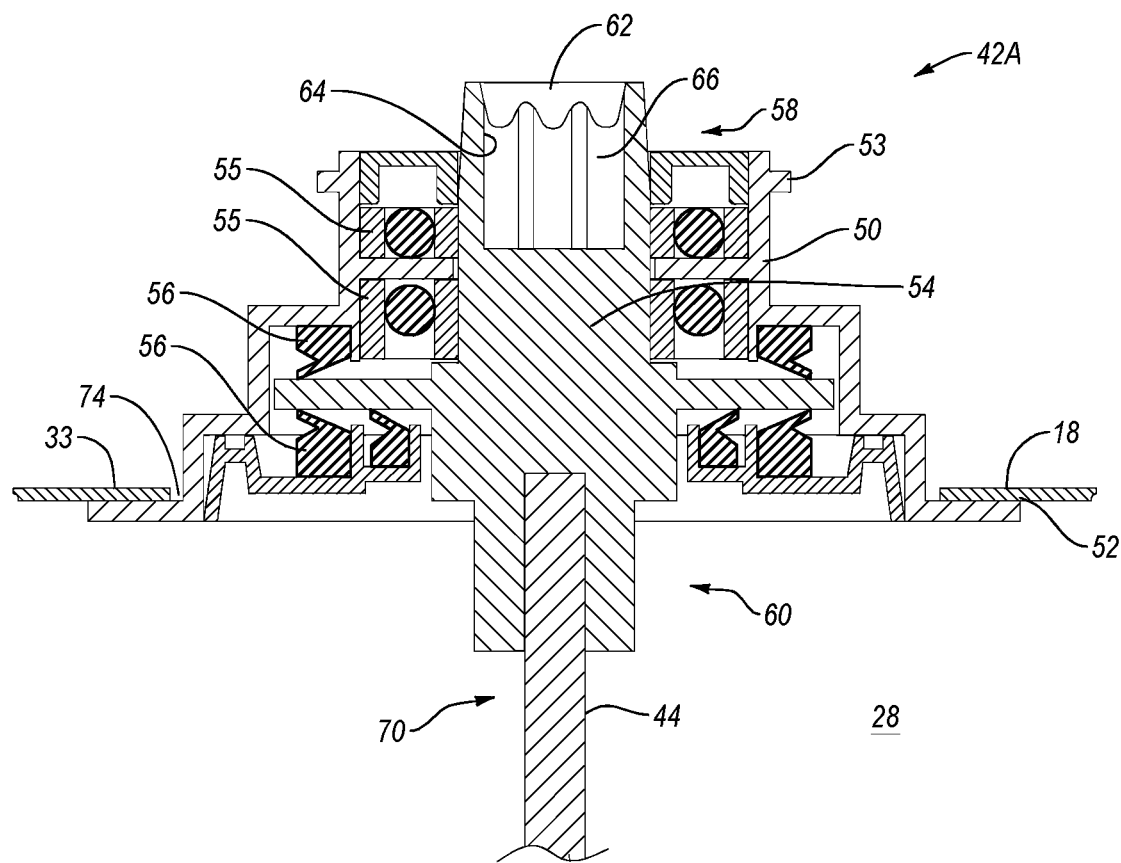
FIG. 4 is a cross sectional side view of the first rotational assembly shown in FIG. 3.

As depicted in FIG. 4, rotational assembly 42A comprises an outer casing 50 having an outwardly projecting annular sealing flange 52 and an outwardly projecting annular mounting flange 53. A hub 54 is rotatably disposed within outer casing 50. One or more bearing assemblies 55 can be disposed between outer casing 50 and hub 54 to permit free and easy rotation of hub 54 relative to casing 50. Likewise, one or more seals 56 can be formed between outer casing 50 and hub 54 so that during use an aseptic seal can be maintained between outer casing 50 and hub 54 as hub 54 rotates relative to outer casing 50. Second end 60 of hub 54 is coupled with a first end 70 of drive line 44. This coupling can be by overmolding, clamp, fastener, or other conventional techniques. Other configurations can also be used.

Rotational assembly 42A is secured to container 18 so that second end 60 of hub 54 communicates with compartment 28. Specifically, in the depicted embodiment container 18 has an opening 74 extending through upper end wall 33. Sealing flange 52 of outer casing 50 is sealed, such as by welding or adhesive, around the perimeter bounding opening 74 so that hub 54 communicates with compartment 28. Flange 52 can be welded on the interior or exterior surface of container 18. In this configuration, outer casing 50 is fixed to container 18 but hub 54, and thus also drive line 44 and impeller 46, can freely rotate relative to outer casing 50 and container 18. As a result of rotational assembly 42A sealing opening 74, compartment 28 is sealed closed so that it can be used in processing sterile fluids.

Turning to FIG. 2, rotational assembly 42B can have the same configuration as rotational assembly 42A and can be mounted to lower end wall 34 of container 18 in the same manner that rotational assembly 42A is mounted to container 18. Like elements between rotational assemblies 42A and 42B are identified by like reference characters. Second end 72 of drive line 44 can be mounted to hub 54 of rotational assembly 42B in the same way that drive line 44 is connected to hub 54 of rotational assembly 42A. As will be discussed below in greater detail, a drive shaft is used to engage and rotate hub 54 of rotational assembly 42A. In the above configuration, a separate drive shaft could also be used to engage and rotate hub 54 of rotational assembly 42B. In other embodiments, hub 54 of rotational assembly 42B need not be directly engaged and rotated by a separate drive shaft and thus opening 62 on hub 54 of rotational assembly 42B can be eliminated.

Impeller 46 comprises a central hub 76 having a plurality of blades 78 radially outwardly projecting therefrom. It is appreciated that a variety of different numbers and configurations of blades 78 can be mounted on hub 76. Hub 76 can be tubular so that hub 76 is slid over drive line 44 and then secured in the desired location by crimping, welding, adhesive or using a set screw, clamp, fastener or other securing technique. In other embodiments, hub 76 can comprise two or more separate members that are secured about drive line 44. In yet other embodiments, drive line 44 can comprise two or more separate members where an end of two of the members can be secured using any desired method on opposing ends of hub 76. Although only one impeller 46 is shown, it is appreciated that impeller 46 can be positioned at any position along drive line 44 and that any number of impellers, such as 2, 3, 4, or more, can be positioned along drive line 44. The impellers disclosed herein and the alternatives discussed relative thereto are examples of mixing elements. Mixing elements, however, also include other structures that can be mounted on drive line 44 that can function to mix fluid when rotated but which would not normally be considered an impeller.

Drive line 44 can be made from a variety of different flexible materials. By way of example and not be limitation, in one embodiment drive line 44 can be made from a braided material such as cable, cord or rope. The braided material can be made from strands that are comprised of metal, polymer or other materials that have desired strength and flexibility properties and can be sterilized. For example, the strands can be made from stainless steel. In other embodiments, drive line 44 can be made from a flexible tube, a single solid core line, a linkage, such as a chain or a linkage of universal joints, or other flexible or hinged members.

As depicted in FIG. 3, impeller assembly 40 is used in conjunction with drive shaft 17. Drive shaft 17 has a first end 84 and an opposing second end 86. Formed at first end 84 is a frustoconical engaging portion 88 that terminates at a circular plate 90. Notches 92 are formed on the perimeter edge of circular plate 90 and are used for engaging drive shaft 17 with a drive motor assembly as will be discussed below.

Formed at second end 86 of drive shaft 362 is driver portion 68. Driver portion 68 has a non-circular transverse cross section complementary to engaging portion 66 of hub 54 (FIG. 4) so that it can facilitate locking engagement within engaging portion 66 of hub 54. In the embodiment depicted, driver portion 68 has a polygonal transverse cross section. However, other non-circular shapes can also be used. It is also appreciated that other releasable locking mechanisms can be used to engage drive shaft 362 with hub 54. For example, a bayonet connection, threaded connection, clamp, or fastener could be used.

Returning to FIG. 1, container station 14 comprises a support housing 100 supported on a cart 102. Support housing 100 has a substantially cylindrical sidewall 104 that extends between an upper end 106 and an opposing lower end 108. Lower end 108 has a floor 110 mounted thereto. As a result, support housing 14 has an interior surface 112 that bounds a chamber 114. An annular lip 116 is formed at upper end 106 and bounds an opening 118 to chamber 114. As discussed above, chamber 114 is configured to receive container assembly 16 so that container 18 is supported therein.

Although support housing 100 is shown as having a substantially cylindrical configuration, in alternative embodiments support housing 100 can have any desired shape capable of at least partially bounding a compartment. For example, sidewall 104 need not be cylindrical but can have a variety of other transverse, cross sectional configurations such as square, rectangular, polygonal, elliptical, or irregular. Furthermore, it is appreciated that support housing 100 can be scaled to any desired size. For example, it is envisioned that support housing 100 can be sized so that chamber 114 can hold a volume of less than 50 liters, more than 1,000 liters or any of the other volumes or range of volumes as discussed above with regard to container 18. Support housing 100 is typically made of metal, such as stainless steel, but can also be made of other materials capable of withstanding the applied loads of the present invention.

With continued reference to FIG. 1, sidewall 104 of support housing 100 has an enlarged access 120 at lower end 108 so as to extend through sidewall 104. A door 122 is hingedly mounted to sidewall 104 and can selectively pivot to open and close access 120. A latch assembly 124 is used to lock door 122 in the closed position. An opening 126, which is depicted in the form of an elongated slot, extends through door 122. Opening 126 is configured to align with ports 31 (FIG. 2) of container assembly 16 when container assembly 16 is received within chamber 114 so that ports 31 project into or can otherwise be accessed through opening 126. In some embodiments, a line for carrying fluid or gas will be couple with port 31 and can extend out of chamber 114 through opening 126. As previously mentioned, any number of ports 31 can be formed on container 18 and thus any number of separated lines may pass out through opening 126 or through other openings formed on support housing 100. Alternatively, different types of probes, inserts, connectors, or the like may be coupled with ports 31 which can be accessed through opening 126 or other openings.

In one embodiment of the present invention means are provided for regulating the temperature of the fluid that is contained within container 18 when container 18 is disposed within support housing 100. By way of example and not by limitation, sidewall 104 can be jacketed so as to bound one or more fluid channels that encircle sidewall 104 and that communicate with an inlet port 130 and an outlet port 132. A fluid, such as water or propylene glycol, can be pumped into the fluid channel through inlet port 130. The fluid then flows in a pattern around sidewall 104 and then exits out through outlet port 132.

By heating or otherwise controlling the temperature of the fluid that is passed into the fluid channel, the temperature of support housing 100 can be regulated which in turn regulates the temperature of the fluid within container 18 when container 18 is disposed within support housing 100. In an alternative embodiment, electrical heating elements can be mounted on or within support housing 100. The heat from the heating elements is transferred either directly or indirectly to container 18. Alternatively, other conventional means can also be used such as by applying gas burners to support housing 100 or pumping the fluid out of container 18, heating the fluid and then pumping the fluid back into container 18. When using container 18 as part of a bioreactor or fermentor, the means for heating can be used to heat the culture within container 18 to a temperature in a range between about 30° C. to about 40° C. Other temperatures can also be used.

As will be discussed below in greater detail, a yoke 140 is centrally mounted on the interior surface of floor 110 of support housing 100. Yoke 140 has a U-shaped slot 142 that is bounded by an inwardly projecting U-shaped catch lip 144. Yoke 140 is configured so that when container assembly 16 is received within chamber 114 of support housing 100, second rotational assembly 42B can be manually slid into slot 142 (FIG. 3) so that mounting flange 53 of second rotational assembly 42B is captured within slot 142 below catch lip 144, thereby securing second rotational assembly 42B to yoke 140 and preventing rotational assembly 42B from being raised vertically relative to yoke 140. It is appreciated that the function of yoke 140 is to releasably engage second rotational assembly 42B and as such, yoke 140 can be in the form of a variety of different slots, clamps, ties, fasteners or the like. It is likewise appreciated that second rotational assembly 42B can be attached to yoke 140 by reaching in through access 120 on sidewall 104 of support housing 100.

As depicted in FIG. 1, docking station 12 comprises a stand 134, an adjustable arm assembly 136 coupled to stand 134 and a drive motor assembly 300 mounted on arm assembly 136. Drive motor assembly 300 is used in conjunction with drive shaft 17 (FIG. 3) and can be used for mixing and/or suspending a culture, solution, suspension, or other liquid within container 18 (FIG. 2). Turning to FIG. 3, drive motor assembly 300 comprises a housing 304 having a front face 305 that extends from a top surface 306 to an opposing bottom surface 308. An opening 310 extends through housing 304 from top surface 306 to bottom surface 308. A tubular motor mount 312 is rotatably secured within opening 310 of housing 304. Upstanding from motor mount 312 is a locking pin 316. A drive motor 314 is mounted to housing 304 and engages with motor mount 312 so as to facilitate select rotation of motor mount 312 relative to housing 304. Drive shaft 17 is configured to pass through motor mount 312 so that engaging portion 88 of drive shaft 17 is retained within motor mount 312 and locking pin 316 of motor mount 312 is received within notch 92 of drive shaft 17. As a result, rotation of motor mount 312 by drive motor 314 facilitates rotation of drive shaft 17. Further discussion of drive motor assembly 300 and how it engages with drive shaft 17 and alternative designs of drive motor assembly 300 are discussed in US Patent Publication No.

2011/0188928, published Aug. 4, 2011 which is incorporated herein in its entirety by specific reference.

Figure 5:
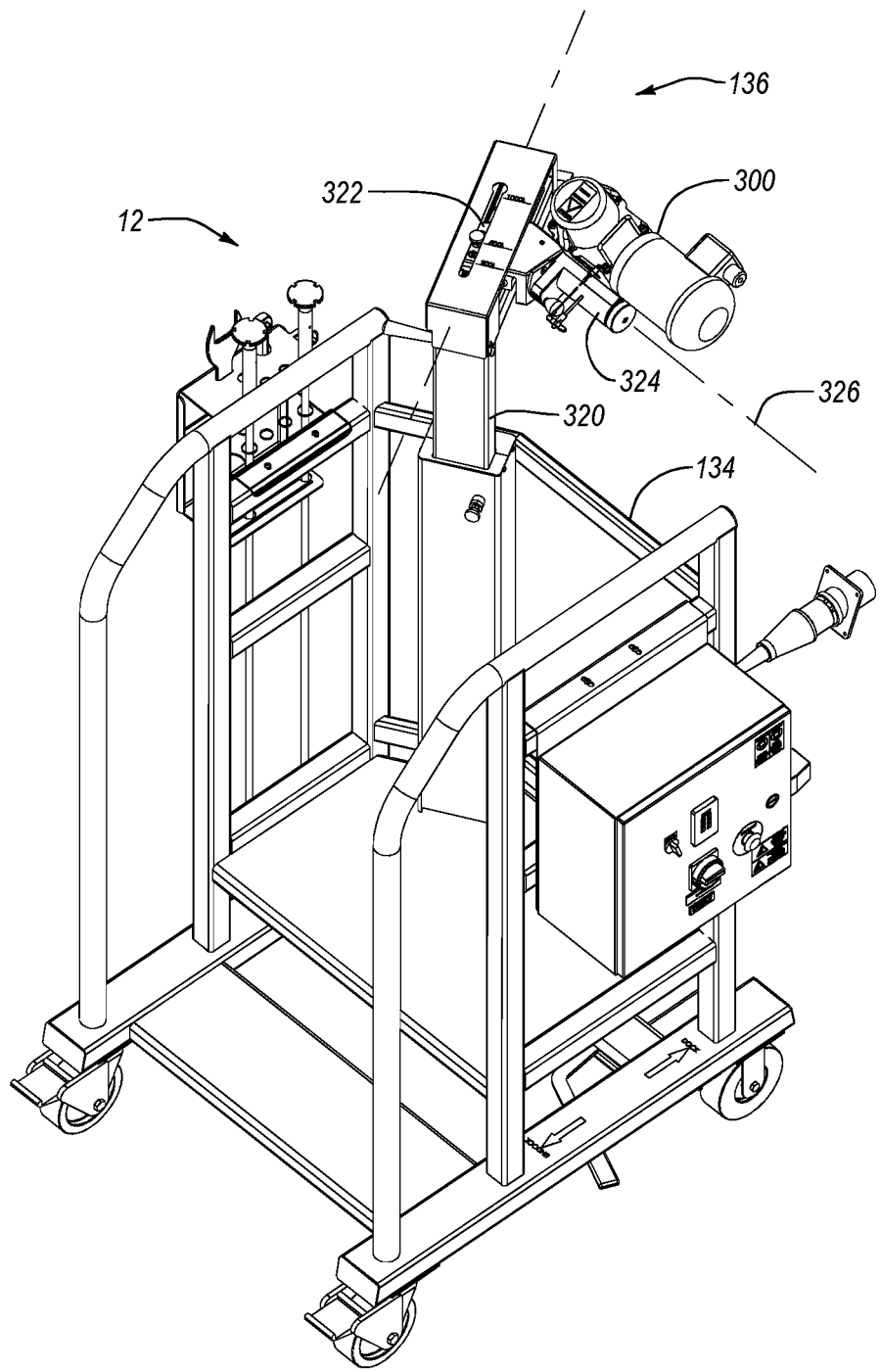
FIG. 5 is a back perspective view of the docking station shown in FIG. 1.

Arm assembly 136 is used to adjust the position of drive motor assembly 300 and thereby also adjust the position of drive shaft 17. As depicted in FIG. 5, arm assembly 136 comprises a first arm 320 mounted to stand 134 that vertically raises and lowers, a second arm 322 mounted to the first arm 320 that slides horizontally back and forth, and a third arm 324 mounted to second arm 322 that rotates about a horizontal axis 326. Drive motor assembly 300 is mounted to third arm 324. Accordingly, by movements of arms 320, 322, and/or 324, drive motor assembly 300 can be positioned in any desired location or orientation relative to support housing 100 and container assembly 16. For example, drive motor assembly 300 can be positioned so that drive shaft 17 is centered and vertically oriented when connected with container assembly 16. In other embodiments, drive shaft 17 can be oriented at an angle, such as in a range between 10° to 30° from vertical when connected with container assembly 16. Further discussion and alternative embodiments with regard to docking station 12, arm assembly 136, and container station 14 is provided in US Patent Publication No. 2011/0310696, published Dec. 22, 2011, which is incorporated herein in its entirety by specific reference.

During use, container station 14 and docking station 12 are removably coupled together as shown in FIG. 1. One example of how docking station 12 and container assembly 16 can be coupled together is disclosed in US Patent Publication No. 2011/0310696 which was previously incorporated by reference. Other methods can also be used. Either before or after coupling together container station 14 and docking station 12, container assembly 16 is positioned within chamber 114 of support housing 100 and second rotational assembly 42B is secured to yoke 140 as discussed above.

In this position, arm assembly 136 is used to properly position drive motor assembly 300 so that first rotational assembly 42A can be coupled with drive motor assembly 300. Specifically, as depicted in FIG. 3, housing 304 of drive motor assembly 300 has a U-shaped receiving slot 330 that is recessed on a front face 305 and bottom surface 308 so as to communicate with opening 310 extending through housing 304. Receiving slot 330 is bounded by an inside face 332 on which a U-shaped catch slot 334 is recessed. As shown in FIG. 1, a door 336 is hingedly mounted to housing 304 and selectively closes the opening to receiving slot 330 from front face 305. As depicted in FIG. 3, to facilitate attachment of rotational assembly 42A to housing 304, with door 336 rotated to an open position, rotational assembly 42A is horizontally slid into receiving slot 330 from front face 305 of housing 304 so that mounting flange 53 that is radially outwardly extending from the upper end of rotational assembly 42A is received and secured within catch slot 334. First rotational assembly 42A is advanced into receiving slot 330 so that opening 62 of rotational assembly 42A aligns with the passage extending through motor mount 312. Door 336 (FIG. 1) is then moved to the closed position and secured in place by a latch or other locking mechanism so that first rotational assembly 42A is locked to drive motor assembly 300.

Figure 6:
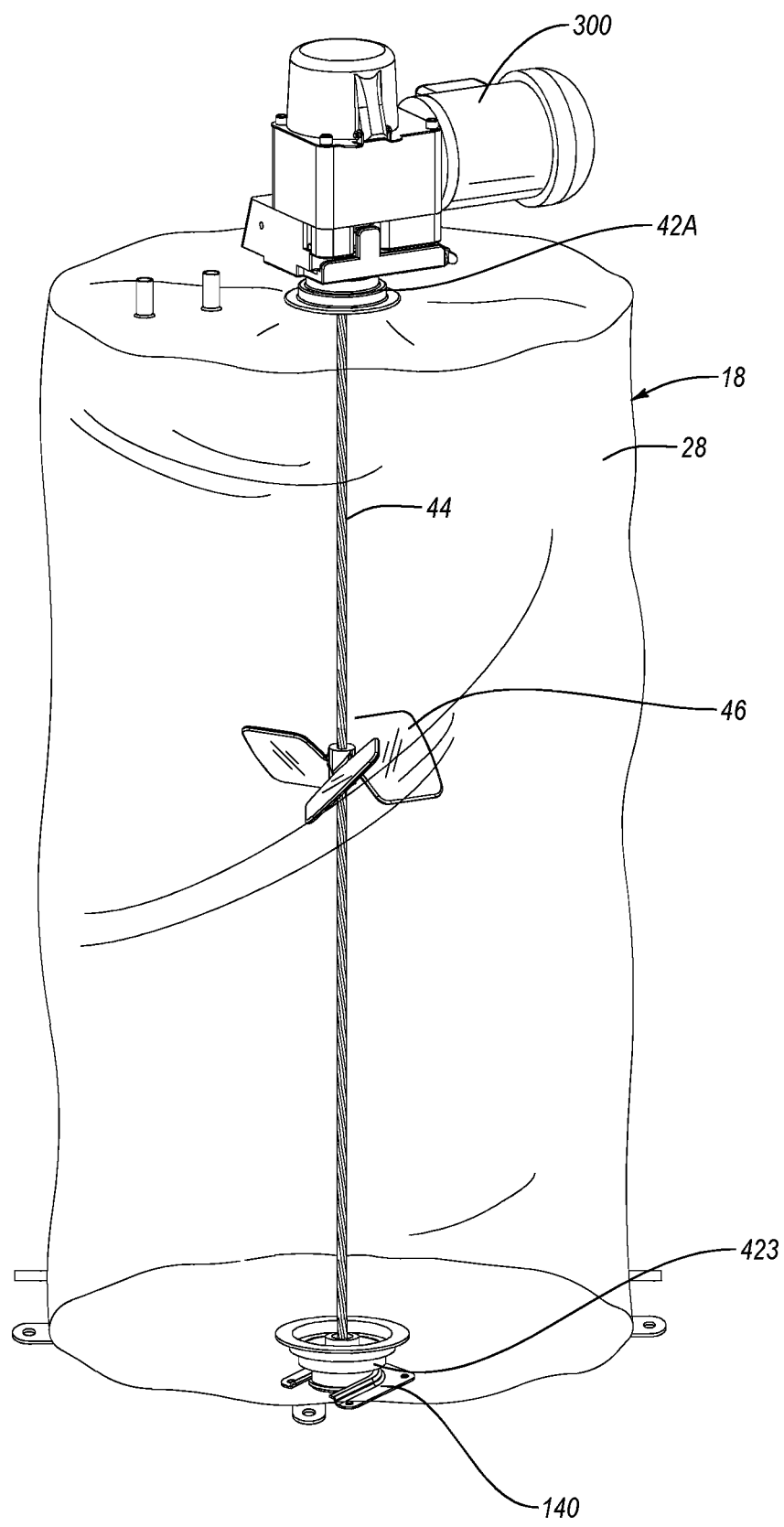
FIG. 6 is a perspective view of the container assembly shown in FIG. 2 coupled with the drive motor assembly and yoke shown in FIG. 1.

Rotational assemblies 42A and 42B are now secured to drive motor assembly 300 and yoke 140, respectively, as shown in FIG. 6. Arm assembly 136 (FIG. 5) can now be used to remove any slack from or to tension flexible drive line 44 by raising drive motor assembly 300 to which rotational assembly 42A is coupled. Likewise, arm assembly 136 can be used to adjust the orientation of drive line 44. For example, by adjusting the position of drive motor assembly 300, drive line 44 can be adjusted so as to be centered within support housing 100 and vertically oriented or drive line 44 can be oriented at an angle, such as in a range between 10° to 30° from vertical. Other positions and orientations can also be used.

Once first rotational assembly 42A is secured to drive motor assembly 300, drive shaft 17 can be advanced down through motor mount 312 of drive motor assembly 300 and into opening 62 of rotational assembly 42A so that drive shaft 17 engages with hub 54. Fluid and other components can be delivered into container 18. Drive motor 324 can be activated so as to rotate drive shaft 17 which in turn begins to rotate hub 54, drive line 44 and impeller 46. Where container 18 is functioning as a bioreactor or fermentor, cells or microorganisms along with nutrients and other standard components can be added to container 18. Rotation of impeller 46 facilitates mixing and/or suspension of the fluid and components contained within container 18. Where drive line 44 is made of a material that flexes under torsion, such as a flexible cable, cord, solid core line or the like, drive line 44 will typically be able to axially twist along the length thereof. That is, first end 70 will begin to rotate concurrently with the rotation of hub 54 of first rotational assembly 42A but second end 72 and hub 54 of second rotational assembly 42A will not begin to rotate until drive line 44 has sufficiently twisted along its length so that second end 72 produces a torsion force on hub 54 of second rotational assembly 42A sufficient to overcome the frictional resistance on hub 54. Impeller 46 also produces resistance against the fluid within container 18 which results in twisting of drive line 44 during rotation. In other embodiments, such as where drive line 44 is a type of linkage, axle twisting of drive line 44 may be negligible.

In one embodiment, at least a portion of drive line 44 is sufficiently flexible so that the flexible portion of drive line 44 can be twisted under torsion about longitudinal axis 48 of drive line 44 over an angle of at least 15°, 25°, 45°, 90°, 180°, 360°, 720° or more without plastic deformation of drive line 44. In other embodiments, at least a portion of drive line 44 is sufficiently flexible so that the flexible portion of drive line 44 can be bent or folded relative to a linear longitudinal axis 48 (FIG. 2) of drive line 44 over an angle α (FIG. 3) of at least 15°, 25°, 45°, 90°, 135°, 180° or more without plastic deformation of drive line 44. Expressed in other terms, drive line 44 or the flexible portion of drive line 44 can have a bend radius wrapped 180° without plastic deformation in a range between about 2 cm to about 100 cm with about 6 cm to about 80 cm, about 10 cm to about 60 cm, or about 10 cm to about 40 cm being more common. Other flexibilities can also be used. It is appreciated that the entire length of drive line 44 need not be flexible. For example, a percentage of the entire length of drive shaft 44, such as at least or not to exceed 30%, 40%, 50%, 60%, 70%, 80% or more of drive shaft 44, could be flexible while the remainder is rigid or at least more rigid.

In an alternative method of use as previously mentioned, a second drive shaft could be coupled with hub 54 of second rotational assembly 42B though a hole formed in floor 110 of support housing 100. In this embodiment, both ends 70 and 72 of drive line 44 could be concurrently rotated although there may still be some twisting of drive line 44 along a central length or adjacent to impeller 46.

In mixing system 10, docking station 12 is used which includes arm assembly 136. In this design, docking station 12 can be coupled with any number of different container stations 14 having a container assembly 16 therein. In an alternative embodiment, however, docking station 12 can be eliminated and arm assembly 136 can be mounted directly onto support housing 100. Alternative examples of arm assemblies and how they can be mounted onto support housing 100 is disclosed in U.S. patent application Ser. No. 13/659,616, filed Oct. 24, 2012 (US Patent Publication No. 2013/0101982, published Apr. 25, 2013), which is incorporate herein in its entirety by specific reference.

Figure 7:
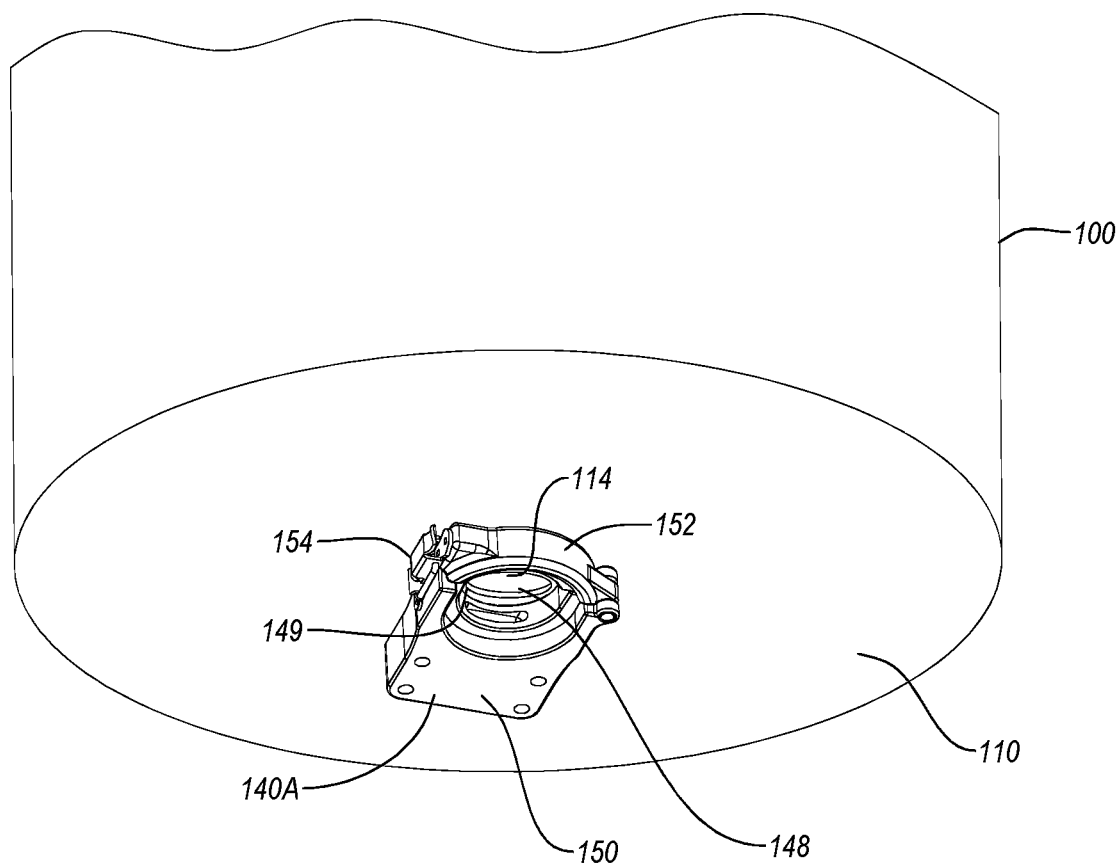
FIG. 7 is a bottom perspective view of an alternative embodiment of the support housing shown in FIG. 1 with a yolk mounted on the exterior surface of the floor.

In the above discussed embodiment depicted in FIG. 1, yoke 140 is mounted on the interior surface of floor 110 of support housing 100 for engaging with second rotational assembly 42B (FIG. 2). In an alternative embodiment as depicted in FIG. 7. A yoke 140A can be mounted on the exterior surface of floor 110 of support housing 100. A hole 148 centrally extends through floor 100 so as to communicate with chamber 114. In this embodiment, yoke 140A has an opening 149 that is bounded between a body 150 and a locking arm 152 hingedly mounted thereto. During use, with locking arm 152 in an open position, the free end of second rotational assembly 42B (FIG. 2) is passed down through hole 148 so as to be received within opening 149. Locking arm 152 is then moved to the closed position, as shown in FIG. 7, and secured in place by a latch 154. In this configuration, the end of second rotational assembly 42B is secured to yoke 140A. It is appreciated that yokes 140 and 140A can come in a variety of other configurations and need only be able to releasably engage the second rotational assembly. In still other embodiments, the yoke need not be secured to support housing 100 but can be located on a separate structure at a position below support housing 100. Second rotational assembly 42B can be configured to pass down through hole 148 and engage with the yoke.

In one embodiment of the present invention, means are provided for holding the lower end 24 of container 18 stationary while flexible drive line 44 is rotated within compartment 28 of container 18. Examples of this means includes yoke 140 mounted on the interior surface of floor 110, yoke 140A mounted on the exterior surface of floor 110 and yoke 140A mounted on a separate structure located below floor 110.

Figure 8:
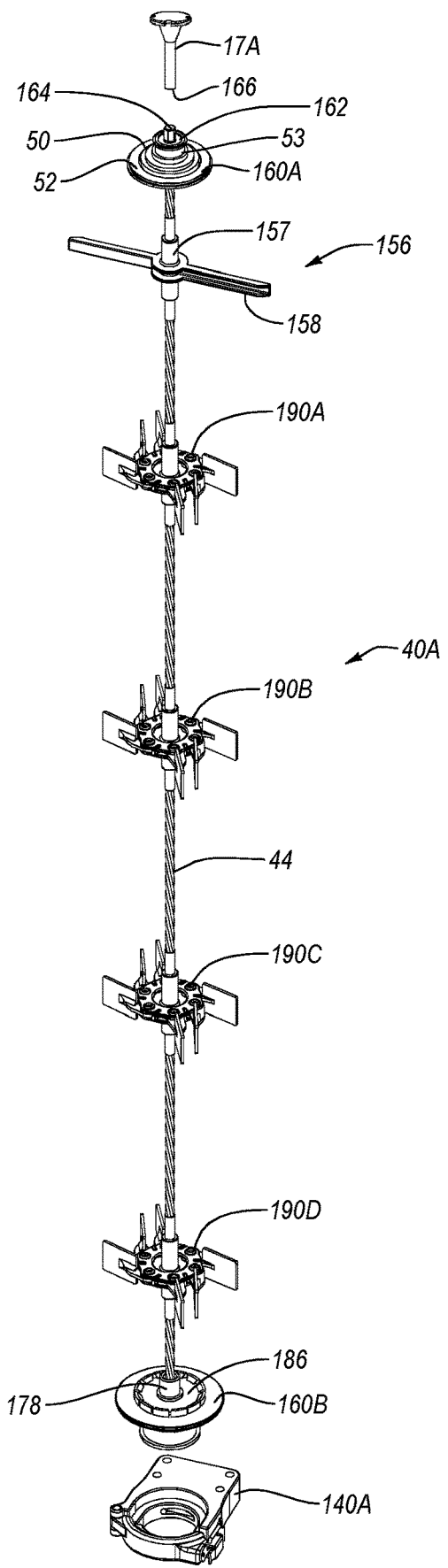
FIG. 8 is a perspective view of an alternative embodiment of an impeller assembly that can be used with the container shown in FIG. 2.

Depicted in FIG. 8 is an alternative embodiment of an impeller assembly 40A. Like elements between impeller assemblies 40 and 40A are identified by like reference characters. Impeller assembly 40A comprises a first rotational assembly 160A and a second rotational assembly 160B with drive line 44 extending therebetween. First rotational assembly 160A has substantially the same configuration as first rotational assembly 42A and includes outer casing 50 having sealing flange 52 for securing to container 18 and mounting flange 53. First rotational assembly 160A has a hub 162 that rotates relative to casing 50. However, in contrast to having an opening 62 (FIG. 4) located at the end thereof, hub 162 includes an outwardly projecting stem 164. Stem 164 has a non-circular transverse cross section, such as polygonal, so that a drive shaft 17A having a complementary socket 166, that replaces driver portion 68 (FIG. 3), can securely engage with and rotate hub 162.

Figure 9:
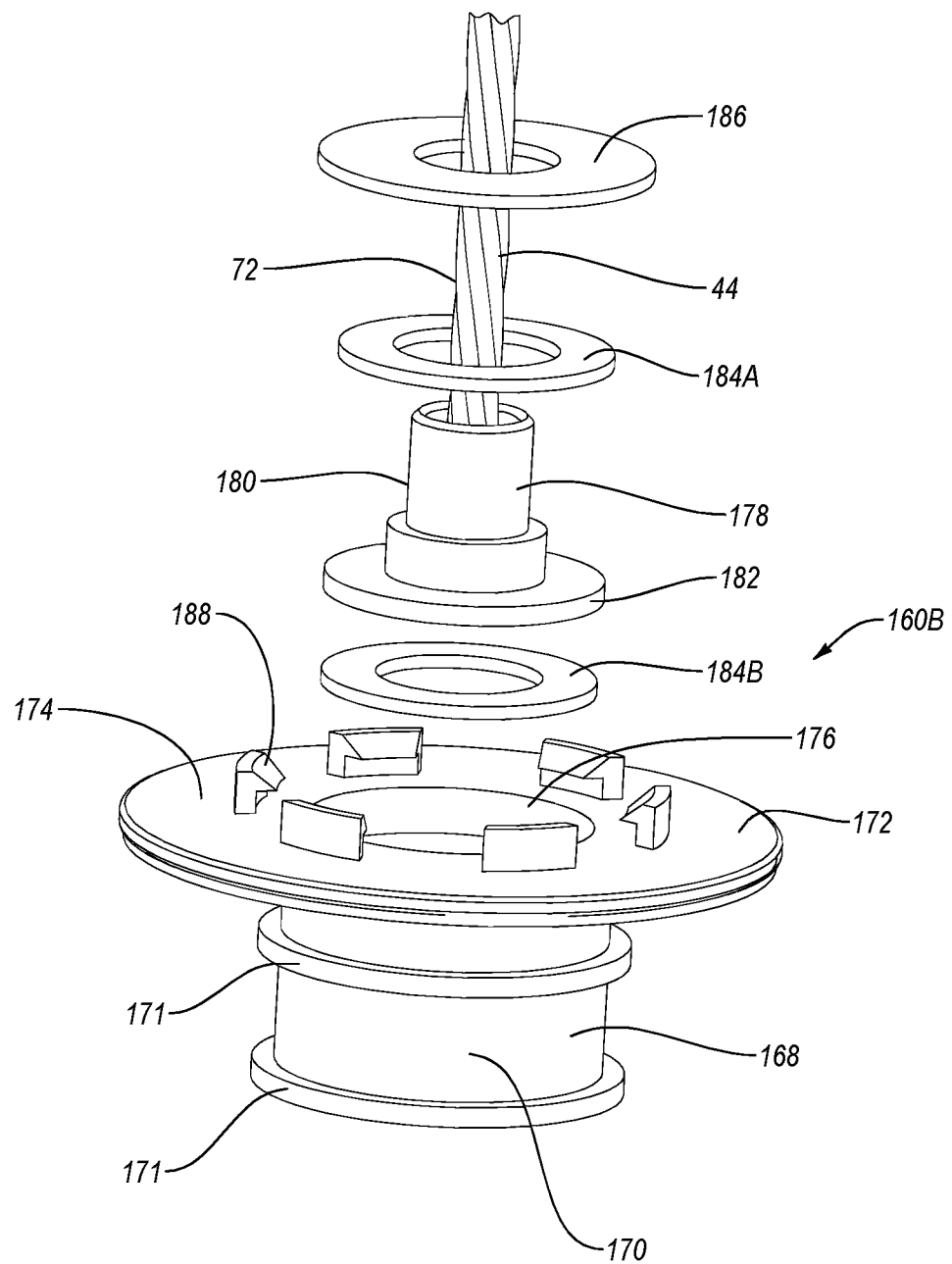
FIG. 9 is an exploded view of the lower rotational assembly shown in FIG. 8.

As depicted in FIG. 9, second rotational assembly 160B comprises an outer casing 168 that includes a cylindrical base 170 having one or more mounting flanges 171 radially outwardly projecting from a lower end thereof and an enlarged annular sealing flange 172 radially outwardly projecting from the upper end thereof. Base 170 and mounting flanges 171 are configured to be engaged by yoke 140A (FIG. 8). Sealing flange 172 is configured to secure to container 18, such as by welding, in the same manner as sealing flange 52 (FIG. 2). Outer casing 168 has a top surface 174 on which a cylindrical blind pocket 176 is formed.

Second rotational assembly 160B also includes a hub 178 having a base 180 to which second end 72 of drive line 44 is secured. Hub 178 also includes an annular flange 182 encircling and radially outwardly projecting from a lower end of base 180. Flange 182 is configured so that it can be rotatably received within blind pocket 176. Annular bearings 184A and 184B, such as roller thrust bearings, are also received within pocket 176 on opposing sides of flange 184 so that hub 178 can freely rotate relative to outer casing 168. A cover plate 186 encircles hub 178 and/or drive line 44 and is positioned over bearing 184A. Cover plate 186 is secured in place by engaging with locking fingers 188 that project from top surface 174 at spaced apart locations around pocket 176. In this configuration, cover plate 186 retains hub 178 within outer casing 168. It is appreciated that because pocket 176 is blind, it is not necessary to position a seal between hub 178 and outer casing 168, although a seal can be used if desired. It is also appreciated that the rotational assemblies can have a variety of other configurations.

Returning to FIG. 8, disposed at an upper end of drive line 44 is a foam breaker 156. Foam breaker 156 includes a hub 157 secured to drive line 44 and a bar 158 that outwardly projects from opposing sides of hub 157. Foam breaker 156 rotates concurrently with drive line 44 to break up foam that is formed at the upper end of container 18. It is appreciated that foam breaker 156 can come in a variety of different configurations.

Figure 10:
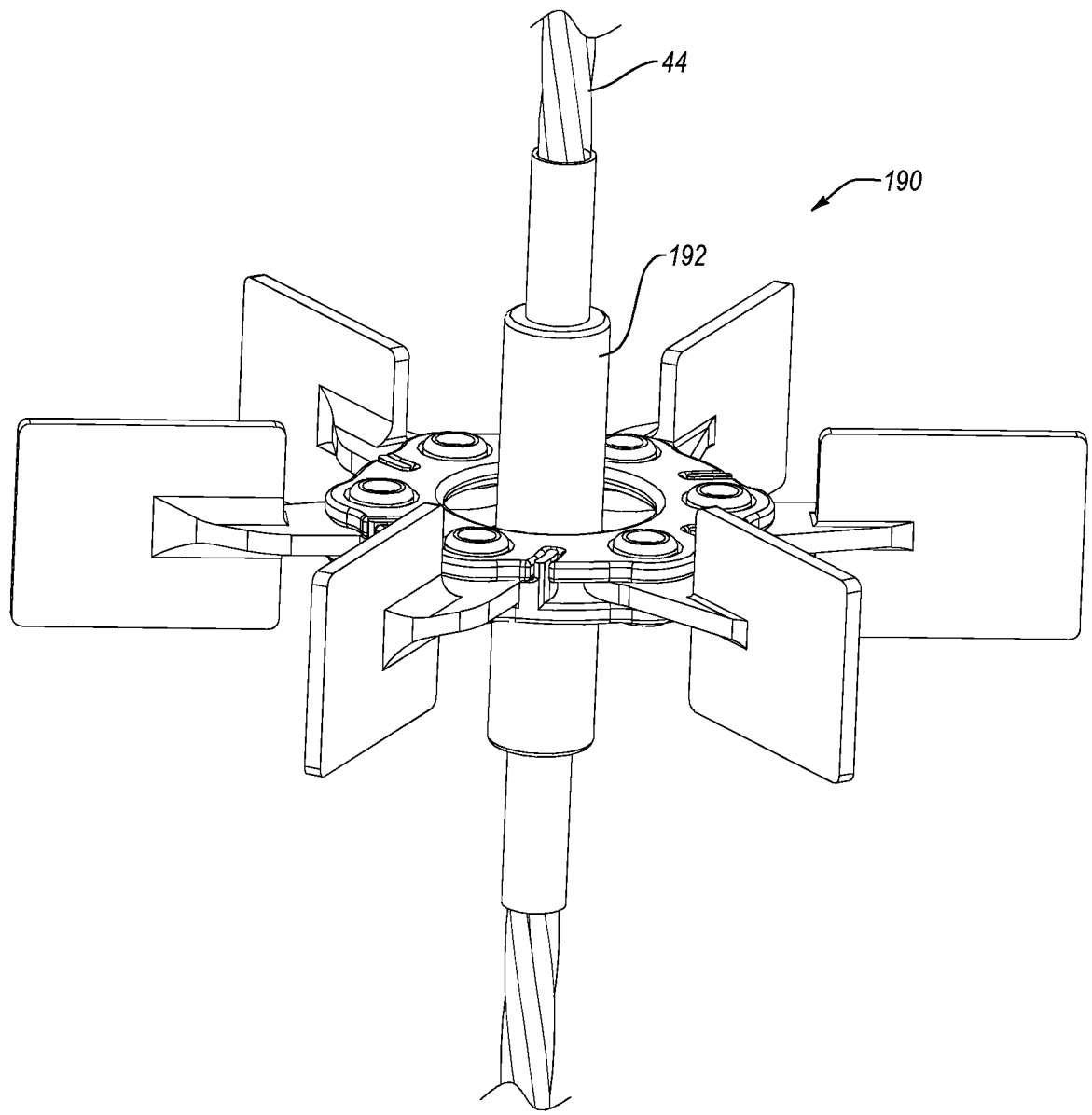
FIG. 10 is an enlarged perspective view of one of the impellers shown in FIG. 8 with the impeller blades in an expanded position.
Figure 11:
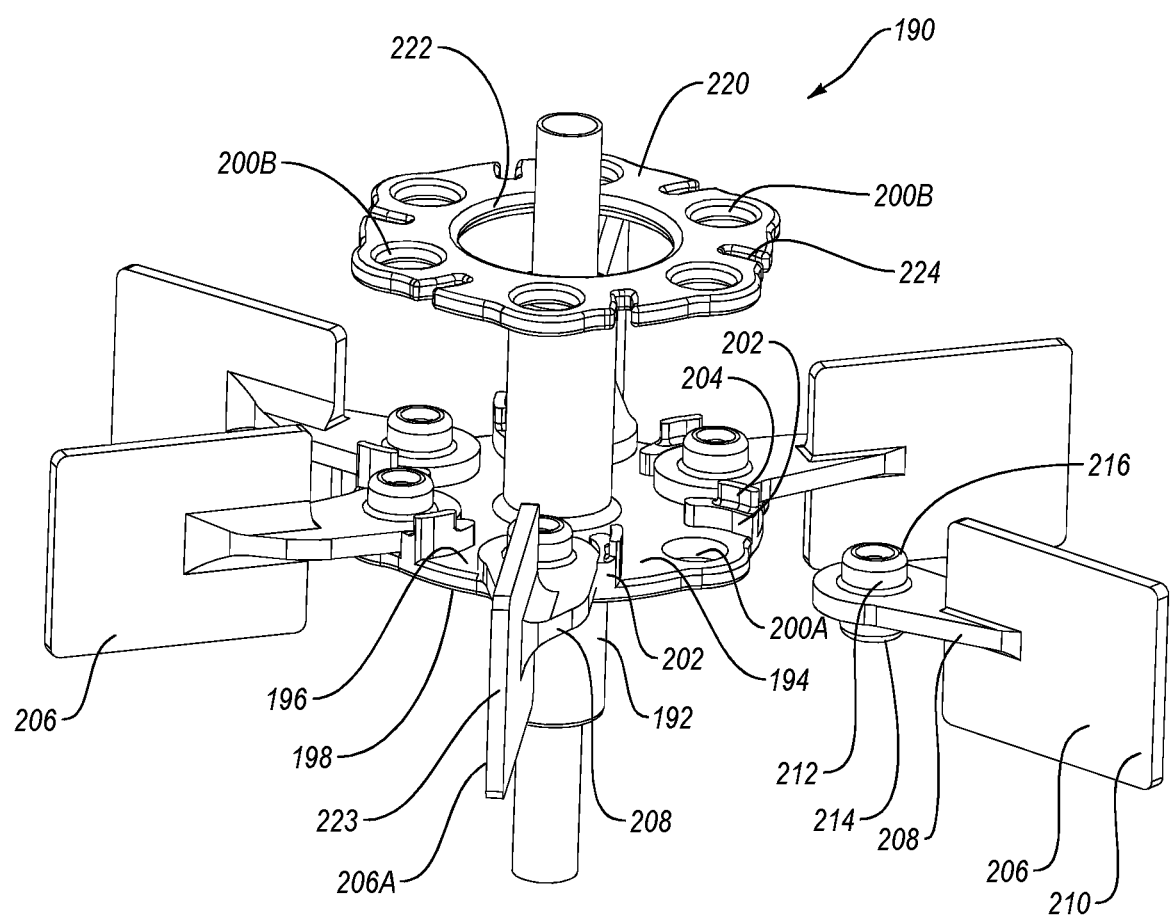
FIG. 11 is a partially exploded perspective view of the impeller shown in FIG. 10.

Also disposed along drive line 44 are a plurality of spaced apart impellers 190A-D. As depicted in FIG. 10, each impeller 190 comprises a tubular hub 192 which can be advanced over drive line 44 and secured in place such as by crimping, clamp, fastener, welding, set screw or the like. As depicted in FIG. 11, a flange 194 encircles and radially outwardly projects from hub 192. Flange 194 has a first side face 196 and an opposing second side face 198 with a plurality of openings 200A extending therethrough adjacent to a perimeter edge of flange 194. Outwardly projecting from first side face 196 are a plurality of spaced apart stops 202 with each stop 202 being disposed adjacent to a corresponding opening 200A. Outwardly projecting from the end of each stop 202 is a key 204.

Impeller 190 also includes a plurality of blades 206. Each blade 206 comprises of an elongated arm 208 having an enlarged blade head 210 located at one end and an axle 212 disposed at the opposing end. Axle 212 has a first end 214 and an opposing second end 216 that project from opposing sides of arm 208. First end 214 of axle 212 is configured to be received within a corresponding opening 200A so that axle 212 can rotate within opening 200A. An annular retainer 220 has a central passage 222 through which hub 192 can be advanced. A plurality of spaced apart openings 200B that are sized to receive second end 216 of axle 212 extend between opposing sides of retainer 220. A plurality of spaced apart keyways 224 are recessed on an outer edge of retainer 220. Retainer 220 is configured to be advanced over hub 192 so that each key 204 is received within a corresponding keyway 224, and second end 216 of each axle 212 is received within a corresponding opening 200B. Retainer 220 can be secured to keys 204 such as by press fit connection, adhesive, welding, fasteners, or the like. Hub 192, flange 194 and retainer 220 combine to form an impeller body to which blades 206 are attached.

Figure 12:
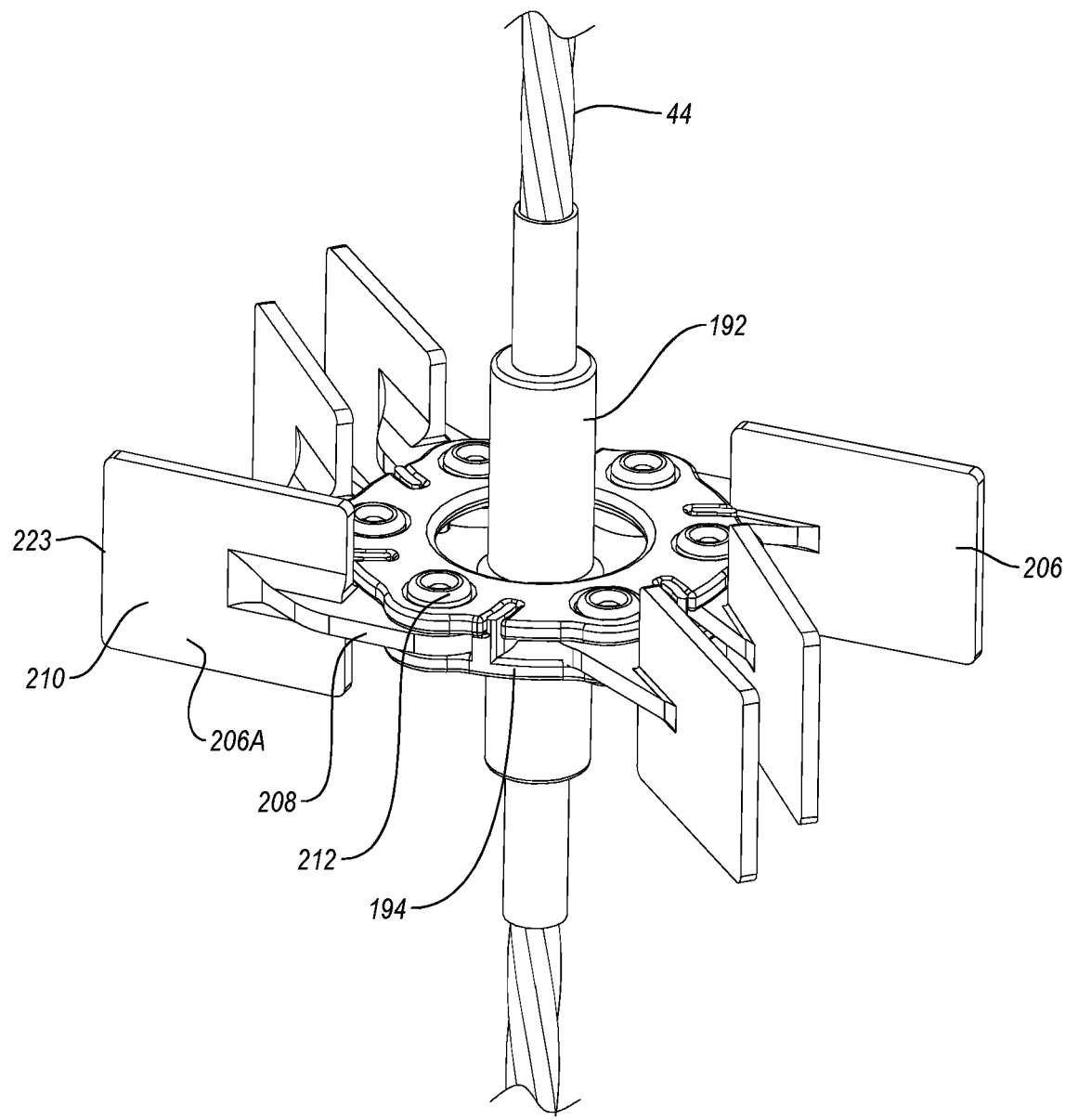
FIG. 12 is a perspective view of the impeller shown in FIG. 10 with some of the blades in a collapsed position.

In the assembled configuration, axle 212 is free to rotate within openings 200A and 200B so that blades 206 are movable between a collapsed position, such as where a blade 206A is folded toward flange 194 in FIG. 12, and an extended position, such as where blade 206A is folded away from flange 194 in FIG. 11. In the extended position, arm 208 hits against stop 202 to prevent further rotation away from the collapsed position. Blades 206 typically radially outwardly project from hub 102 when in the extended position but can project at angles relative to hub 102. In most embodiments, however, an outer tip 223 of blades 206 is spaced farther from hub 192 when in the extended position than when in the collapsed position.

In alternative embodiments, it is appreciated that there are a wide variety of different ways in which blades 206 can be rotatably connected to hub 192. For example, axles 212 could be rigidly fixed to flange 194 and/or retainer 220. Arms 208 could then pivot about axles 212. In another embodiment, axles 212 could be hingedly secured to flange 194 so as to eliminate the need for retainer 220. In addition, both flange 194 and retainer 220 could be integrally formed as a unitary member with hub 192 and blades 206 could be snap fit or otherwise secured therebetween. Other alternatives also exist.

During sterilization, transport, storage, and at other times, in can be desirable to fold up or roll up container 18 into a more compact structure so that it is easier to handle and occupies less space. By making drive line 44 out of a flexible material, this enables drive line 44 to be concurrently folded up or rolled up with container 18. Use of the flexible drive line also eliminates the need for an elongated drive shaft which can be expensive to make and difficult to attach, particularly in low ceiling environments. Furthermore, by making blades 206 movable between the collapsed and extended position, some or all of the blades can be moved to the collapsed position during the folding or rolling up of container 18. Collapsing of the blades enables container 18 to be folded smaller, helps prevents blades 206 from puncturing container 18 and can result in less stress being placed on blade 206. However, as will be discussed below in greater detail, as each impeller 190 is rotated within the fluid contained within container 18, each of blades 206 catch the fluid and automatically move to the expanded position which is a more optimal position for mixing the fluid.

Figure 13:
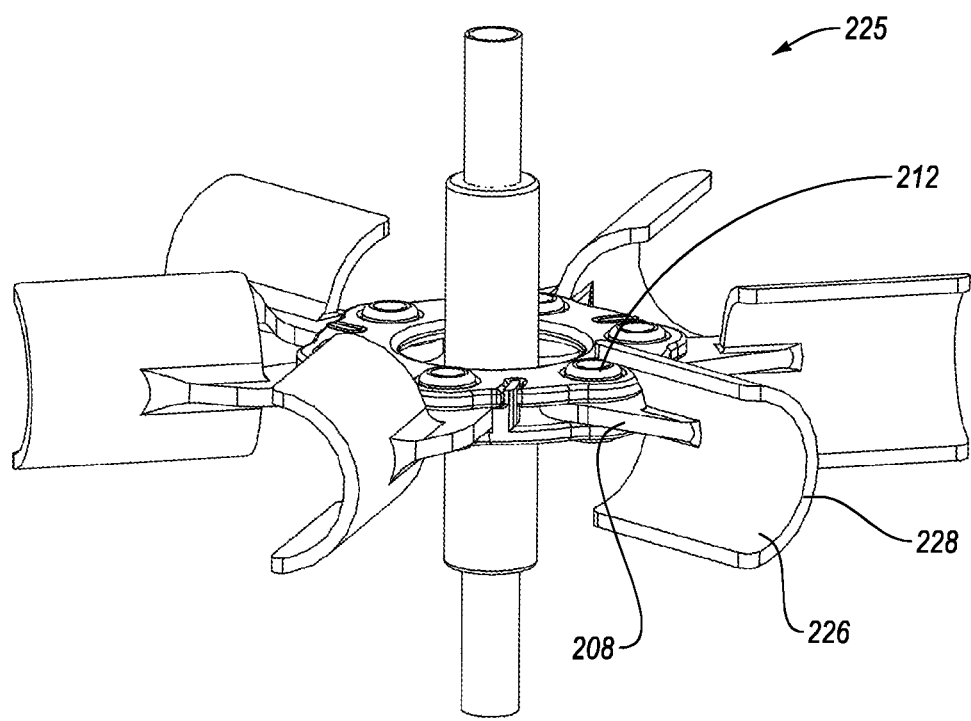
FIG. 13 is a perspective view of an alternative embodiment of an impeller having impeller blades with a different configuration.
Figure 14:
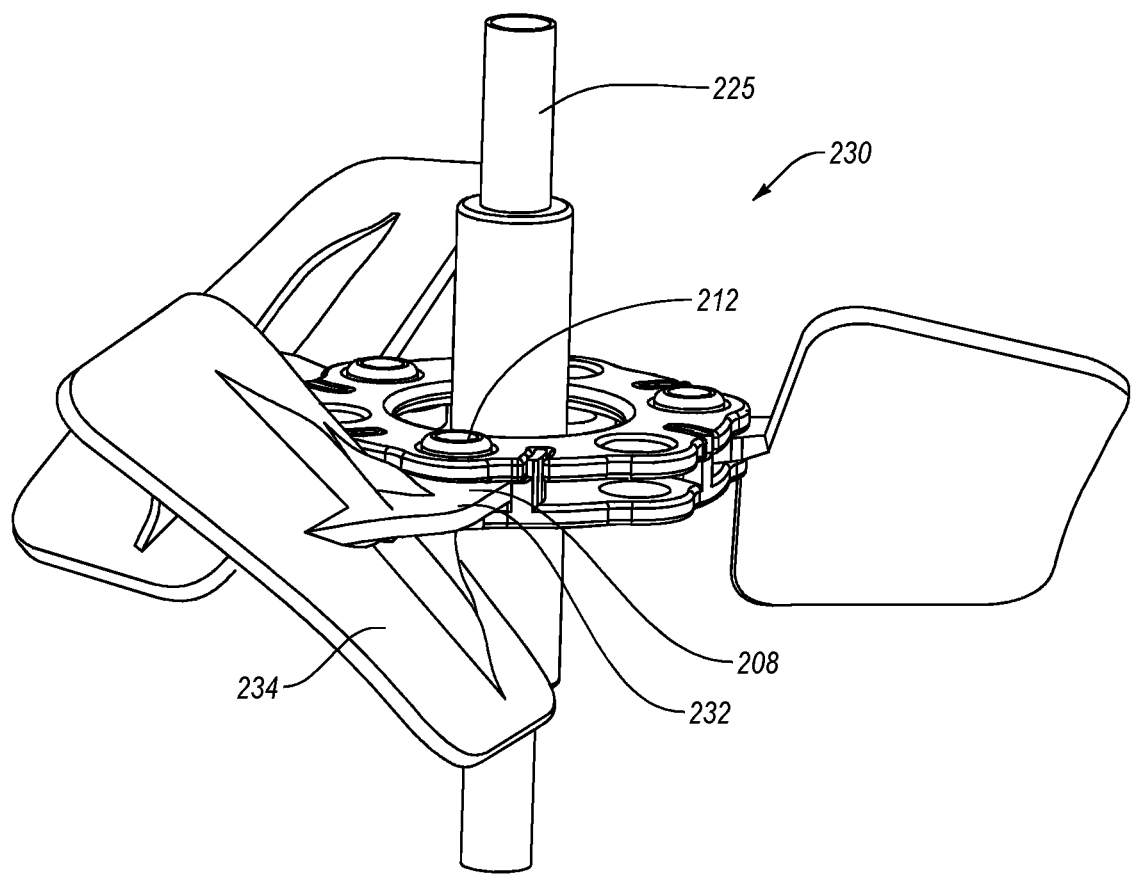
FIG. 14 is a perspective view of another alternative embodiment of an impeller having different impeller blades.

Another benefit of the inventive impeller 190 is that it is a modular system that can be used within a variety of different blade configurations. For example, in the embodiment depicted in FIG. 10, each blade 206 has a blade head 210 having a generally flat rectangular configuration. This configuration of blade is commonly referred to as a Rushton blade. Depicted in FIG. 13 is an impeller 225 with like elements between impeller 190 and impeller 225 being identified by like reference characters. The only difference between impellers 225 and 190 is that in impeller 225, blades 206 have been replaced with blades 226. Blades 226 include arm 208 and axle 212 but in contrast to having a flat rectangular blade head 210, they have a blade head 228 having a curved surface. More specifically, blade head 228 has a length with an arched or substantially semi-circular transverse cross section along the length. Again, each of blades 226 can be moved from a collapsed position to an extended position. Depicted in FIG. 14 is still another embodiment of an impeller 230 having foldable blades 232 with a blade head 234 that slopes relative to the longitudinal axis of hub 192.

In each of impellers 190, 225, and 230, the same impeller body can be used with blades of any desired configuration or size. Furthermore, the exchangeable blades need not be rotatable but can be designed to be fixed in the extended position. Such, modular impellers provide greater flexibility in being able to easily produce impellers having a desired configuration and mixing properties while maintaining a minimum number of stock parts.

Figure 15:
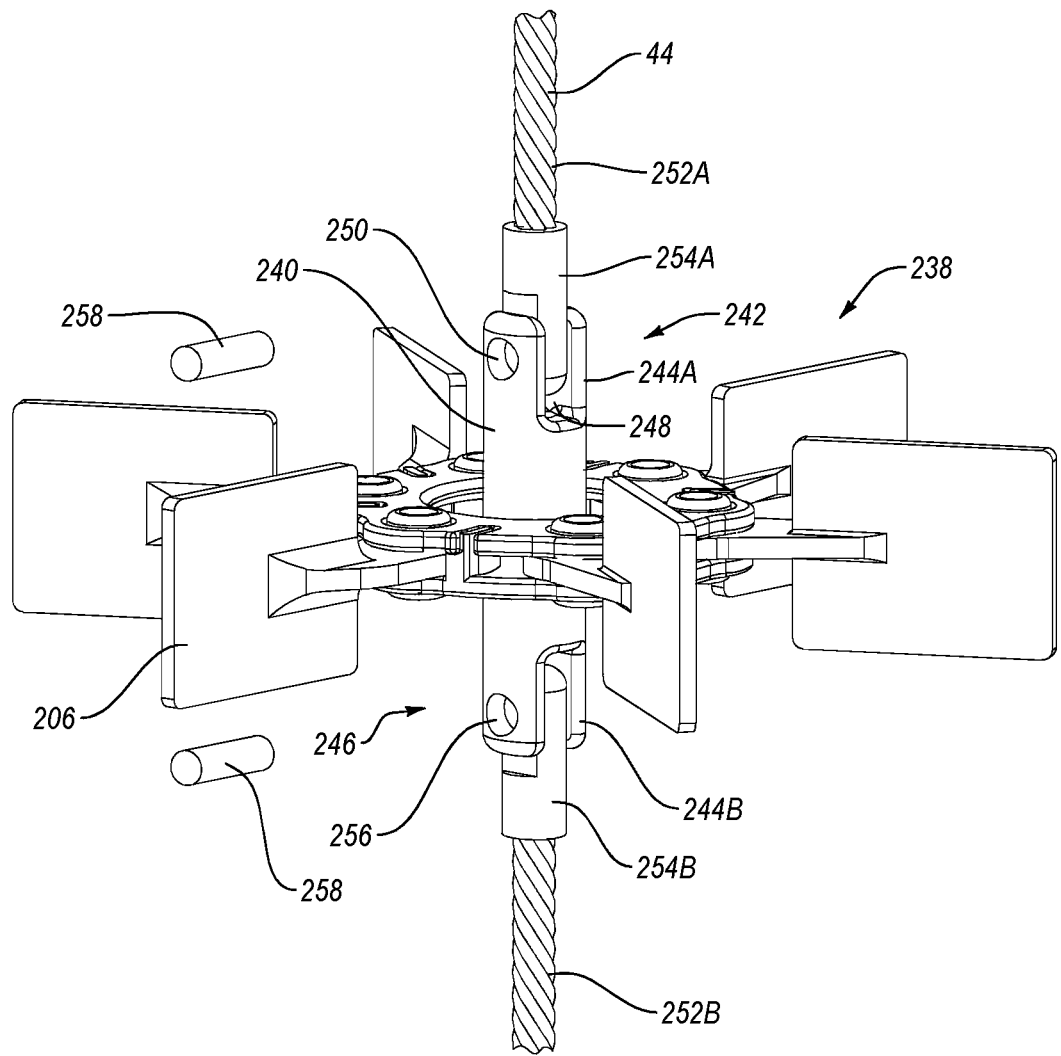
FIG. 15 is a perspective view of an alternative embodiment of an impeller wherein the flexible drive line is hingedly mounted to the impeller.

Depicted in FIG. 15 is an alternative embodiment of an impeller 238 that is hingedly mounted to drive line 44. Like elements between impellers 190 and 238 are identified by like reference characters. Impeller 238 is substantially identical to impeller 190 except that in contrast to hub 192 (FIG. 10) which is tubular and received over drive line 44, impeller 238 includes an elongated hub 240 having a first end 242 with a U-shaped connecter 244A formed thereat and an opposing second end 246 with a U-shape connector 244B formed thereat. Each of connectors 244A and B bound a slot 248 and have an opening 250 transversely extending therethrough. Flexible line 44 is comprised of line portion 252A having connector 254A mounted on the end thereof and line portion 252B having a connector 254B mounted on the end thereof. Each of connecters 254A and B also have an opening 256 transversely extending therethrough. During assembly, connectors 254A and B are received within slots 248 of U-shaped connectors 244A and B, respectively, so that openings 250 and 256 are aligned. Hinge pins 258 are then received within aligned openings 250 and 256 and secured in place so that connectors 254A and B can freely pivot relative to impeller 238. Hinge pins 258 can be attached to connectors 244A and B by being press fit, welded, threaded or using other conventional techniques. In alternative embodiments, it is appreciated that a variety of different unions, hinges, swivels, and the like can be used to hingedly connect line portions 252A and B to opposing ends of hub 240. Furthermore, although impeller 238 is shown having pivotably mounted blades 206, in an alternative embodiment impeller 238 can be formed with fixed blades.

Figure 16:
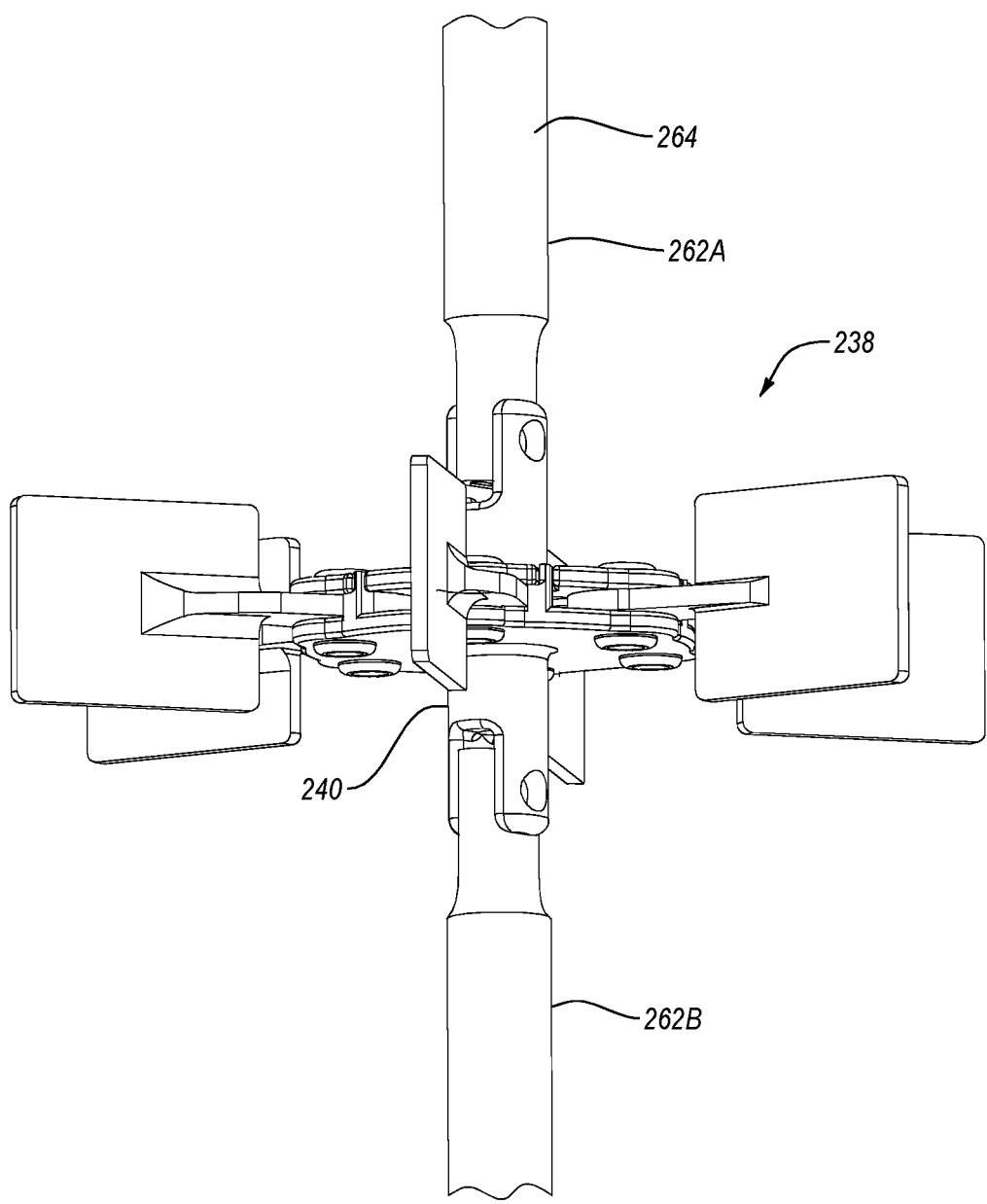
FIG. 16 is a perspective view of an alternative embodiment of an impeller wherein the drive line comprises rigid shaft sections that are hingedly mounted to opposing ends of the impeller.

FIG. 16 again depicts impeller 238. However in contrast to being hingedly coupled to flexible drive line 44, impeller 238 in FIG. 16 is hingedly coupled to line portions 262A and B of a rigid drive line 264. That is, line portions 262A and B can have openings 256 extending therethrough and can be made of shafts, rods or tubes or the like that are comprised of or consist of metal, plastics, composites, or the like that are substantially rigid or have limited flexibility. For example, line portions 262A and B can have a bend radius wrapped 90° that must be greater than 8 meters, 10 meters or 12 meters to prevent plastic deformation.

Figure 17:
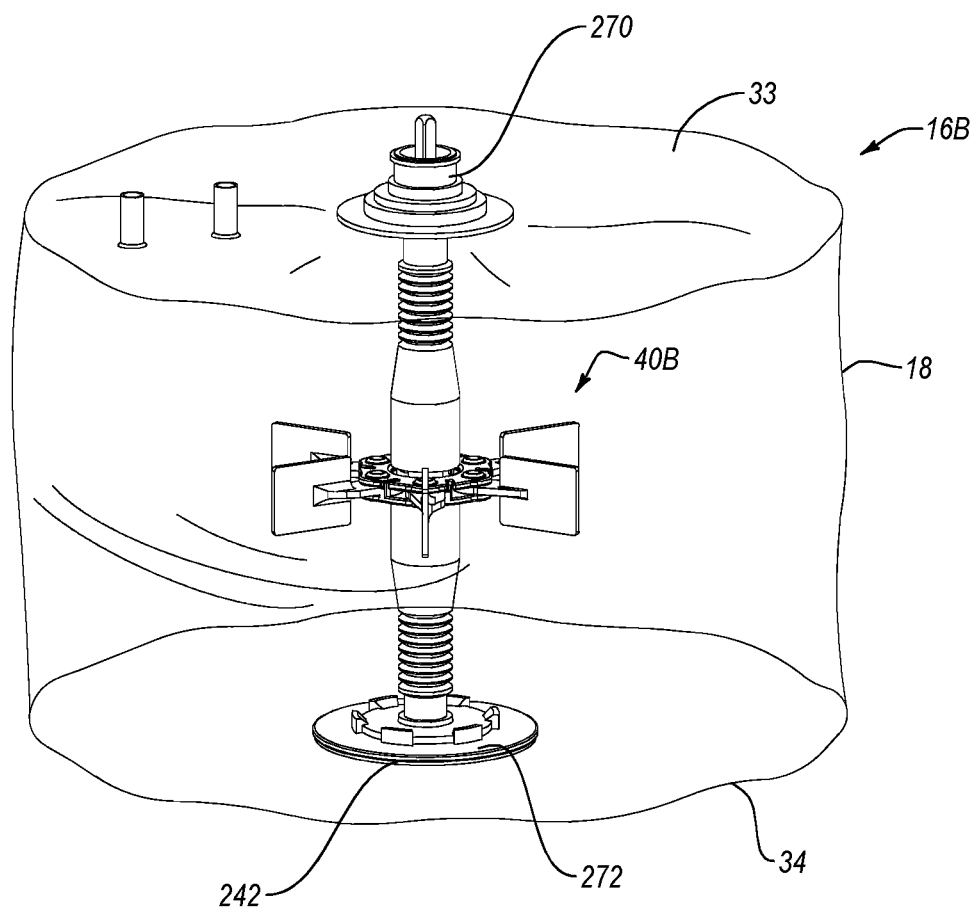
FIG. 17 is a perspective view of an alternative embodiment of a container assembly.
Figure 18:
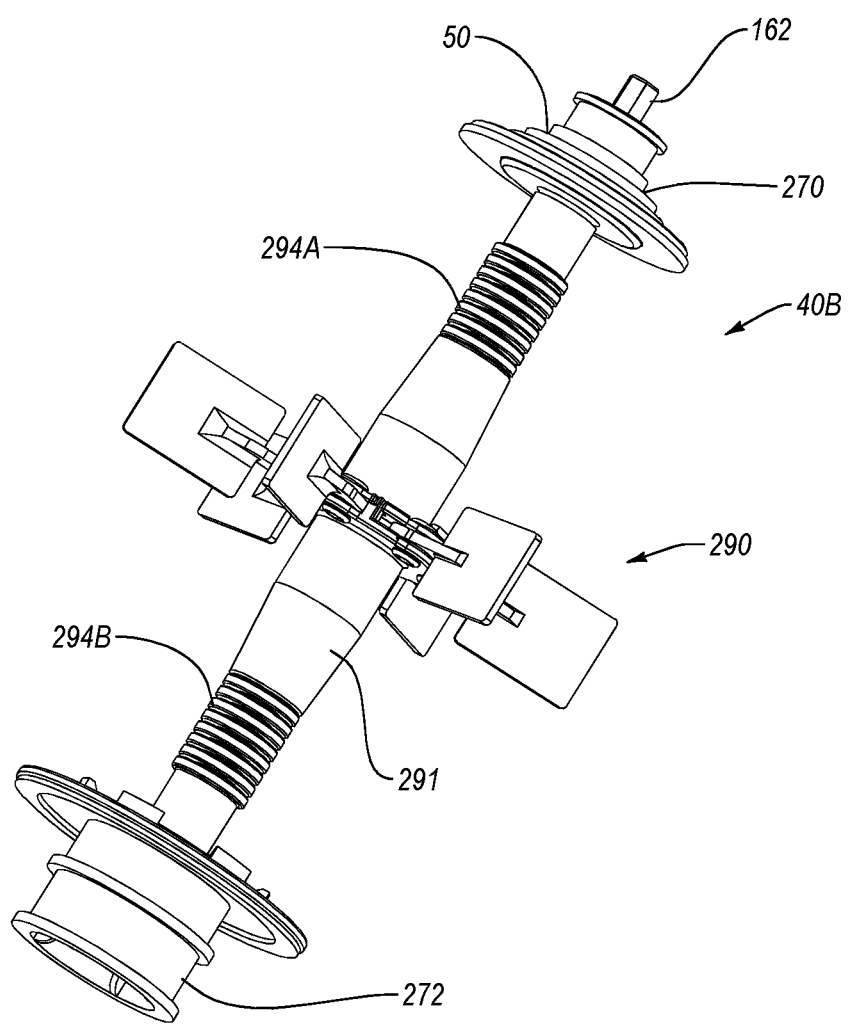
FIG. 18 is a perspective view of the impeller assembly shown in FIG. 17.
Figure 19:
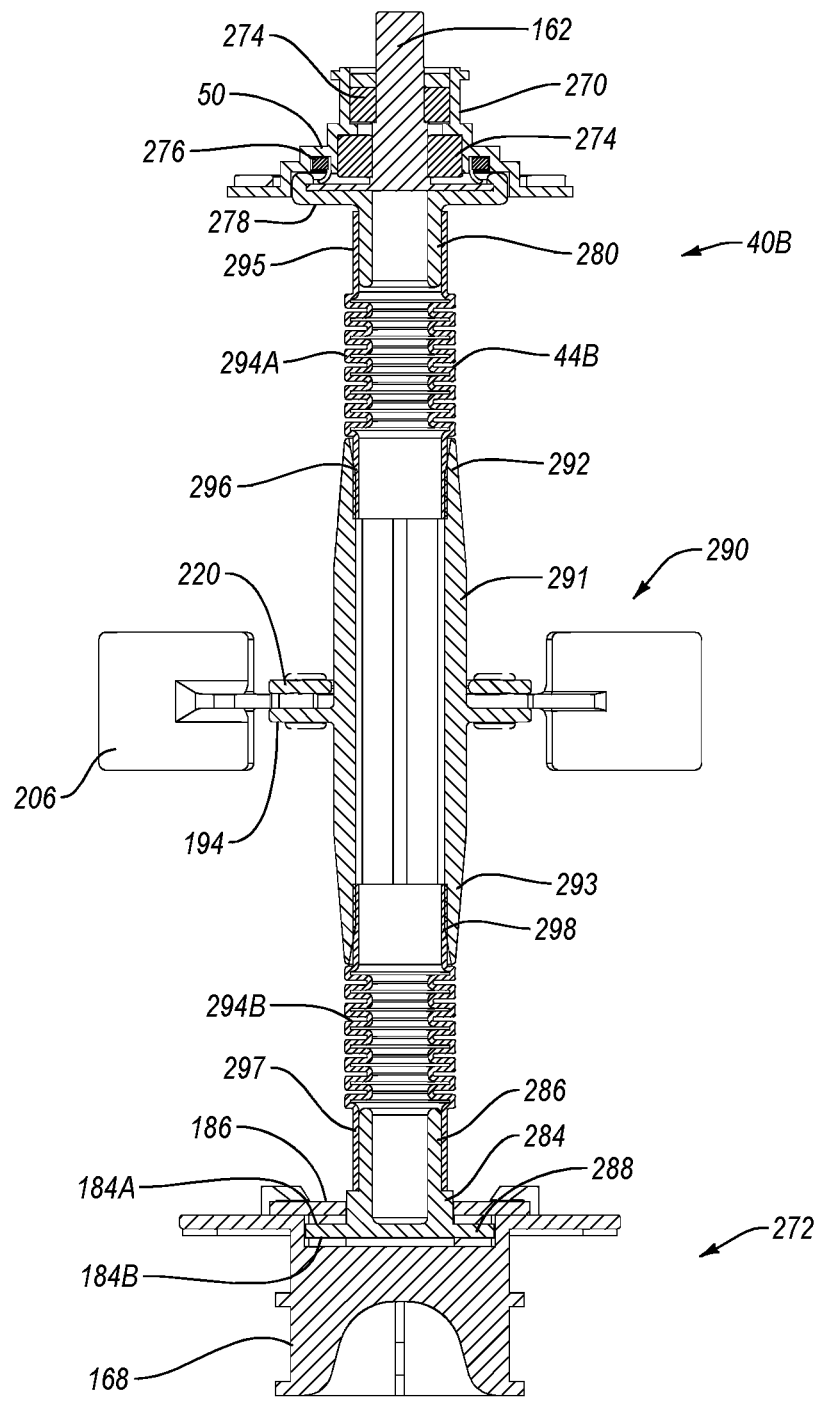
FIG. 19 is a cross sectional side view of the impeller assembly shown in FIG. 18.

Depicted in FIG. 17 is a perspective view of an alternative embodiment of a container assembly 16B that includes an alternative embodiment of a flexible drive line. Container assembly 16B can be operated within support housing 100 (FIG. 1) in substantially the same manner as the other container assemblies discussed herein. Specifically, container assembly 16B comprises container 18 having an impeller assembly 40B coupled thereto. Impeller assembly 40B comprises a first rotational assembly 270 mounted to upper end wall 33 of container 18 and a second rotational assembly 242 mounted to lower end wall 34 of container 18. As depicted in FIGS. 18 and 19, upper rotational assembly 270 comprises outer casing 50 and hub 162 as previously discussed. Various bearing assemblies 274 can be positioned between outer casing 50 and hub 162 to facilitate ease of rotation of hub 162. One or more seals 276 can also be positioned between outer casing 50 and hub 162 to form a liquid-tight seal therebetween. An adapter 278 is coupled with hub 162 and has a stem 280 that projects away from hub 162. In an alternative embodiment, stem 280 can be integrally formed as a unitary structure with hub 162.

Second rotational assembly 272 includes outer casing 168, bearings 184A and B and cover plate 186 as previously discussed. Second rotational assembly 272 also includes a hub 284 having an upwardly extending stem 286 that passes through cover plate 186 and an outwardly projecting flange 288 that is positioned between bearings 184A and B. Located between rotational assemblies 270 and 272 is an impeller 290. Impeller 290 comprises a tubular hub 291 having a first end 292 and an opposing second end 293. Flange 194 encircles and radially outwardly projects from hub 291. Blades 206 hingedly mounted between flange 194 and retainer 220 as previously discussed. In an alternative embodiment, fixed blades can be secured to hub 291 or flange 194.

Drive line assembly 40B also includes a flexible drive line 44B that includes a drive line portion 294A and a drive line portion 294B. Each of drive line portions 294 comprise a flexible tube that can be made of a resiliently flexible plastic or other material. In the depicted embodiments, although not required, the tubes are corrugated so as to increase flexibility. Drive line portions 294 can have the same flexibility as drive line 44 as previously discussed. Drive line portion 294A has a first end 295 that is received over and coupled to stem 280 and an opposing second end 296 that is received within and secured to first end 292 of hub 291. Similarly drive line portion 294B has a first end 297 received over and secured to stem 286 and an opposing second end 298 received within and secured to second end 293 of hub 291. In this configuration, rotation of hub 162 of first rotational assembly 270 facilitates rotation of drive line portions 294A and B, impeller 290, and hub 284 of second rotational assembly 272.

Figure 20:
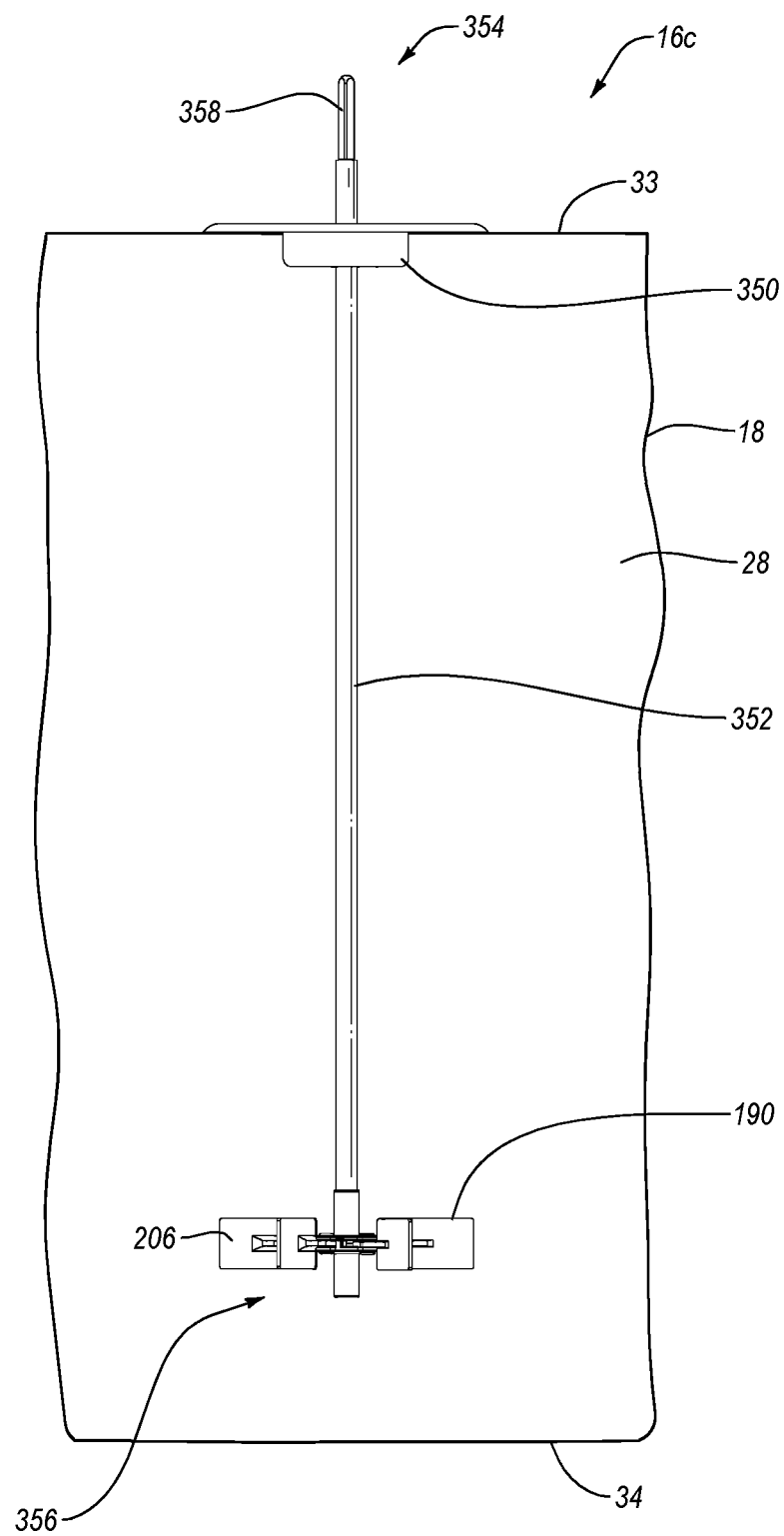
FIG. 20 is an elevational front view of an alternative embodiment of a container assembly containing a rigid drive shaft with an impeller having pivotable blades.

Although the above discussed embodiments primarily disclose the use of impellers having pivotable blades with flexible drive lines, it is appreciated that the inventive impellers of the present invention can also be used with rigid drive shafts. For example, depicted in FIG. 20 is a container assembly 16C that includes container 18. A dynamic seal 350 is mounted on upper end wall 33. A rigid drive shaft 352 passes through dynamic seal 350 and has a first end 354 disposed outside of container 18 and an opposing second end 356 disposed within container 18. Dynamic seal 350 enables drive shaft 352 to freely rotate relative to container 18 while forming an aseptic seal between container 18 and drive shaft 352. A driver portion 358, which can have a polygonal or other non circular transverse cross section or some other engaging surface, can be formed at first end 354 so that a drive motor can engage with and rotate drive shaft 352.

Mounted on second end 356 of drive shaft 352 is impeller 190 as previously discussed herein. Rotation of drive shaft 356 causes blades 206 to move to the expanded position and mix the fluid within container 18. Impeller 190 can be replaced with the other impellers discussed herein having pivotable blades and can incorporate other alternative configurations as discussed herein. Again, as a result of pivotable blades 206, container 18 can be more fully collapsed around impeller 190 while minimizing risk of damage to container 18 and to blades 206.

Figure 21:
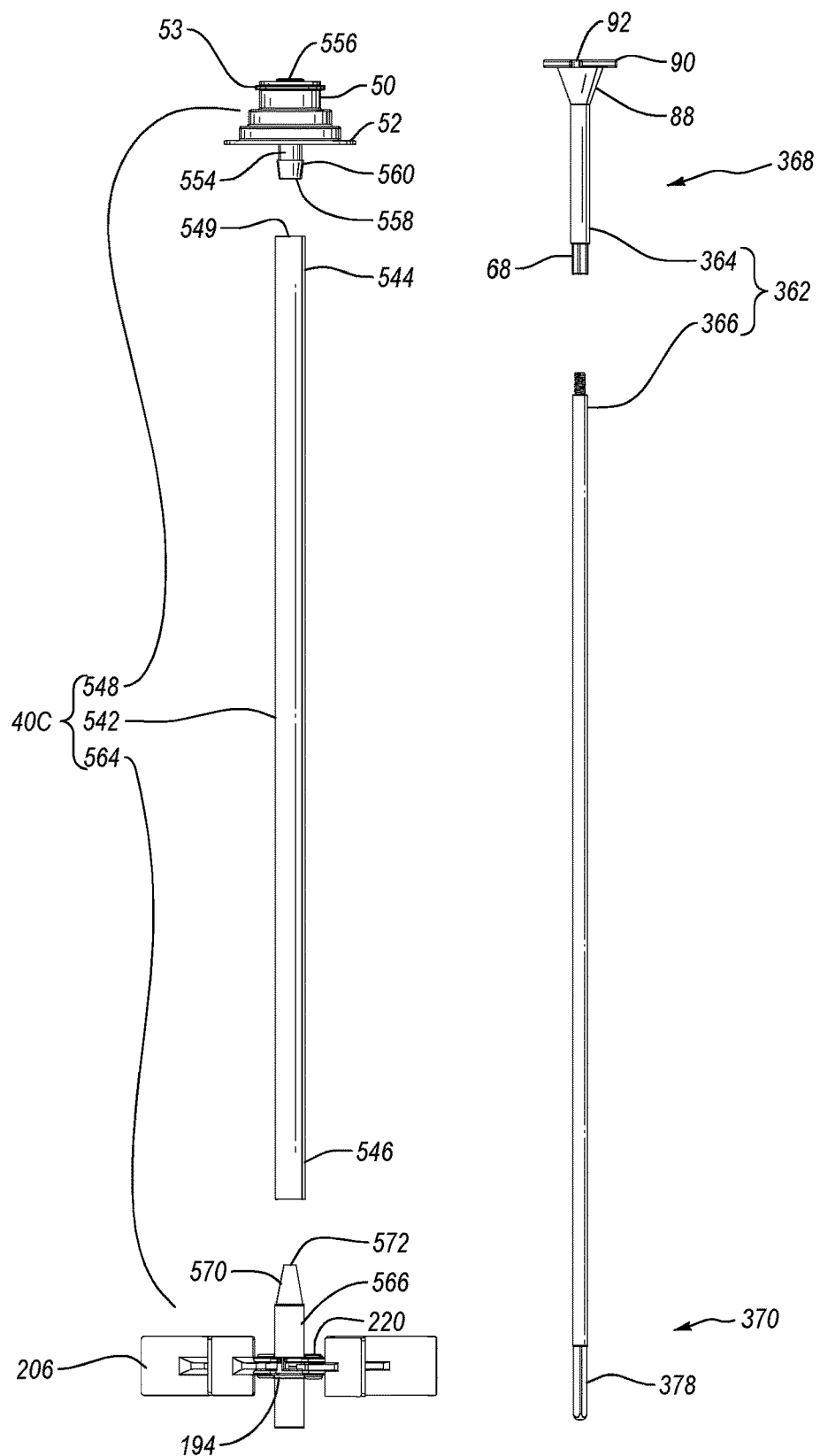
FIG. 21 is an elevational front view of an alternative embodiment of an impeller assembly that can be used with a rigid drive shaft.

Depicted in FIG. 21 is another alternative embodiment of mixing system that incorporates an impeller with pivotable or foldable blades. The mixing system includes an impeller assembly 40C that comprises an elongated tubular connector 542 having a rotational assembly 548 mounted at one end and an impeller 564 or other mixing element mounted on the opposing end. More specifically, tubular connector 542 has a first end 544 and an opposing second end 546 with a passage 549 that extends therebetween. In one embodiment, tubular connector 542 comprises a flexible tube, such as a polymeric tube, having the same flexibility as discussed above with regard to drive line 44. As such, tubular connector 542 can comprise a flexible drive line as claimed herein. In other embodiments, tubular connector 542 can comprise a rigid tube or other tubular structure.

Rotational assembly 548 is mounted to first end 544 of tubular connector 542. Rotational assembly 548 comprises outer casing 50 having an outwardly projecting annular sealing flange 52 and an outwardly projecting mounting flange 53 as previously discussed. A tubular hub 454 is rotatably disposed within outer casing 50. One or more bearing assemblies, as previously discussed, can be disposed between outer casing 50 and hub 554 to permit free and easy rotation of hub 554 relative to casing 50. Likewise, one or more seals, as previously discussed, can be formed between outer casing 50 and hub 554 so that during use an aseptic seal can be maintained between outer casing 50 and hub 554.

Hub 554 has an interior surface 556 that bounds an opening 558 extending therethrough. Interior surface 556 includes an engaging portion having a polygonal or other non-circular transverse cross section so that driver portion 68 of drive shaft 362, as also shown in FIG. 21, passing through opening 558 can engage the engaging portion and facilitate rotation of hub 554 by rotation of drive shaft 362. Hub 554 can also comprise a tubular stem 560 projecting away from outer casing 50. Hub 554 can couple with first end 544 of tubular connector 542 by stem 560 being received within first end 544. A pull tie, clamp, crimp or other fastener can then be used to further secure stem 560 to tubular connect 542 so that a liquid tight seal is formed therebetween. Other conventional connecting techniques can also be used.

Impeller 564 comprises a central hub 566 having blades 206 pivotably coupled thereto through the use of flange 194 and retainer 220 as previously discussed with regard to FIG. 11. Alternative embodiments as discussed herein with regard to other impellers having pivotable blades can also be incorporated into impeller 564. Hub 566 has a first end 570 with a blind socket 572 formed thereat. Socket 572 typically has a noncircular transverse cross section, such as polygonal, so that it can engage a driver portion 378 of drive shaft 362. Accordingly, when driver portion 378 is received within socket 572, driver portion 378 engages with impeller 564 such that rotation of drive shaft 362 facilities rotation of impeller 564.

Impeller 564 can be attached to connector 542 by inserting first end 570 of hub 566 within connector 542 at second end 546. A pull tie, clamp, crimp, or other type of fastener can then be cinched around second end 546 of connector 542 so as to form a liquid tight sealed engagement between impeller 564 and connector 542.

Rotational assembly 548 is secured to container 18 in substantially the same manner that rotational assembly 42 was secured to container 18, as previously discussed with regard to FIG. 2, so that tubular connector 542 and impeller 564 extend into or are disposed within compartment 28 of container 18.

In general drive shaft 362 comprises a head section 364 and a shaft section 366 that can be coupled together by threaded connection or other techniques. Head section 364 has substantially the same configuration as drive shaft 17 discussed with regard to FIG. 3 and thus like features head section 364 and drive shaft 17 will be identified by like reference characters. Alternatively, drive shaft 362 can be formed as a single piece member or from a plurality of attachable sections. Drive shaft 362 has a first end 368 and an opposing second end 370. Formed at first end 368 is a frustoconical engaging portion 88 as previously discussed with regard to FIG. 3. Formed at second end 370 of drive shaft 362 is driver portion 378. Driver portion 378 has a non-circular transverse cross section so that it can facilitate locking engagement within hub 466 of impeller 464. In the embodiment depicted, driver portion 378 has a polygonal transverse cross section. However, other non-circular shapes can also be used. Driver portion 68 is also formed along drive shaft 362 toward first end 368. Driver portion 68 also has a non-circular transverse cross section and is positioned so that it can facilitate locking engagement within the engaging portion of rotational assembly 448.

During use, container 18 having impeller assembly 40C coupled thereto is received within support housing 100 (FIG. 1) and rotational assembly is secured to drive motor assembly 300 as previously discussed with regard to FIG. 3. Drive shaft 362 is advanced down through motor mount 312, hub 454 of rotational assembly 548, tubular connecter 542 and into hub 566 of impeller 564. As a result of the interlocking engagement of driver portions 378 and 68 with hubs 566 and 554, respectively, rotation of drive shaft 362 by drive motor assembly 300 facilitates rotation of hub 554, tubular connecter 542 and impeller 564 relative to outer casing 50 of rotational assembly 548 and container 18. The rotation of impeller 564 causes blades 206 to move to the expanded position and mix the fluid within container 18.

It is appreciated that impeller assembly 40C, drive shaft 362 and the discrete components thereof can have a variety of different configuration and can be made of a variety of different materials. Alternative embodiments of and further disclosure with respect to impeller assembly 40C, drive shaft 362, and the components thereof are disclosed in U.S. Pat. No. 7,384,783, issued Jun. 10, 2008 and US Patent Publication No. 2011/0188928, published Aug. 4, 2011 which are incorporated herein in their entirety by specific reference.

Figure 22:
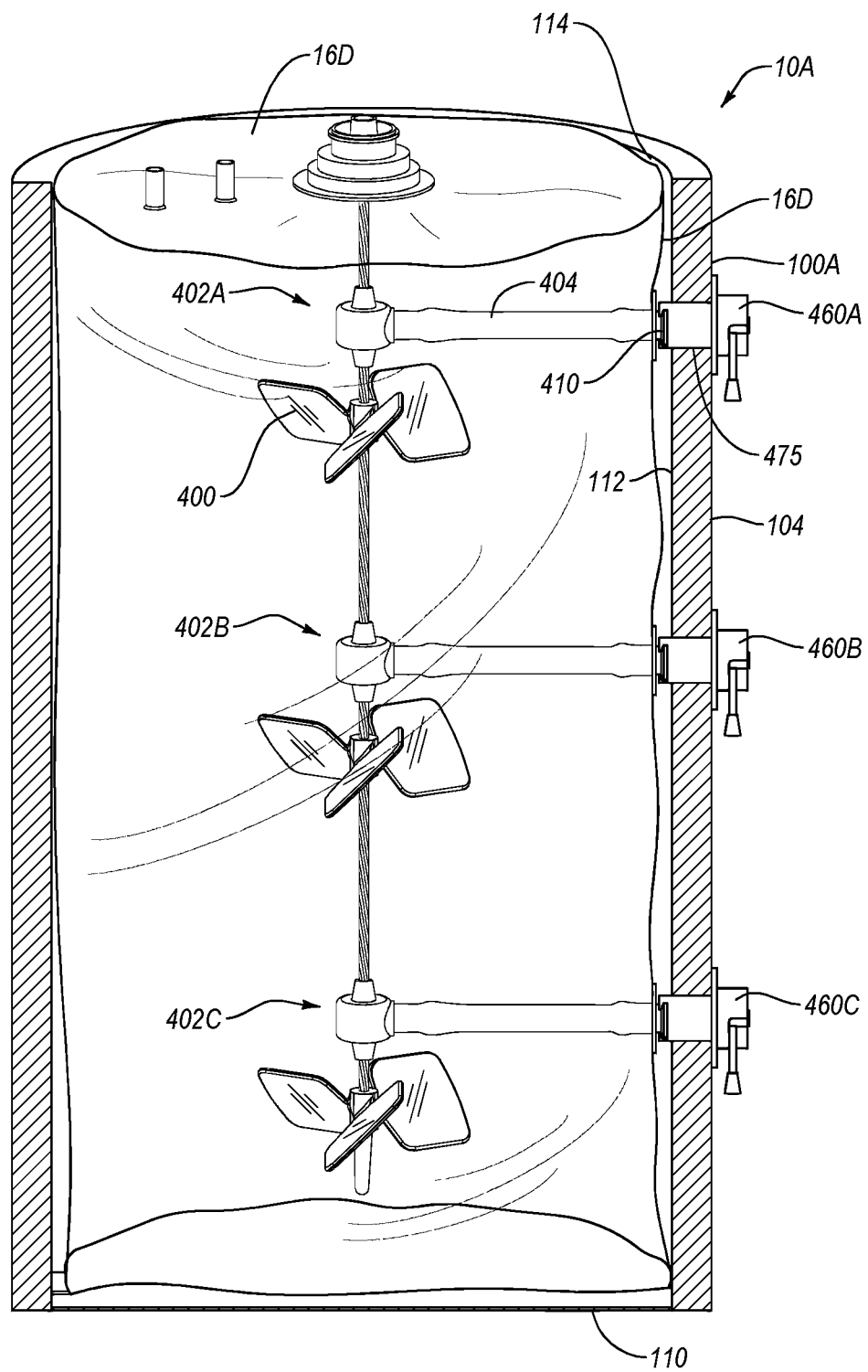
FIG. 22 is a partial cross sectional front view of an alternative embodiment of a fluid mixing system that includes a container assembly with lateral support assemblies and a support housing.

In the prior discussed embodiments incorporating the flexible drive line, the flexible drive line is supported by being secured to both the upper end wall and lower end wall of the container. In an alternative embodiment, the flexible drive line can be supported and stabilized by being secured to the upper end wall of the container and at one or more locations along the length of the flexible drive line. For example, depicted in FIG. 22 is an alternative embodiment of a fluid mixing system 10A incorporating features of the present invention. Fluid mixing system 10A comprises a container assembly 16D at least partially disposed within the compartment of a support housing 100A. Like elements between container assembly 16 and 16A and between support housing 100 and 100A are identified by like reference characters. Furthermore, disclosure and alternative embodiments as previously discussed with regard to container 16 and support housing 100 are also applicable to corresponding elements of container assembly 16A and support housing 100A.

Figure 23:
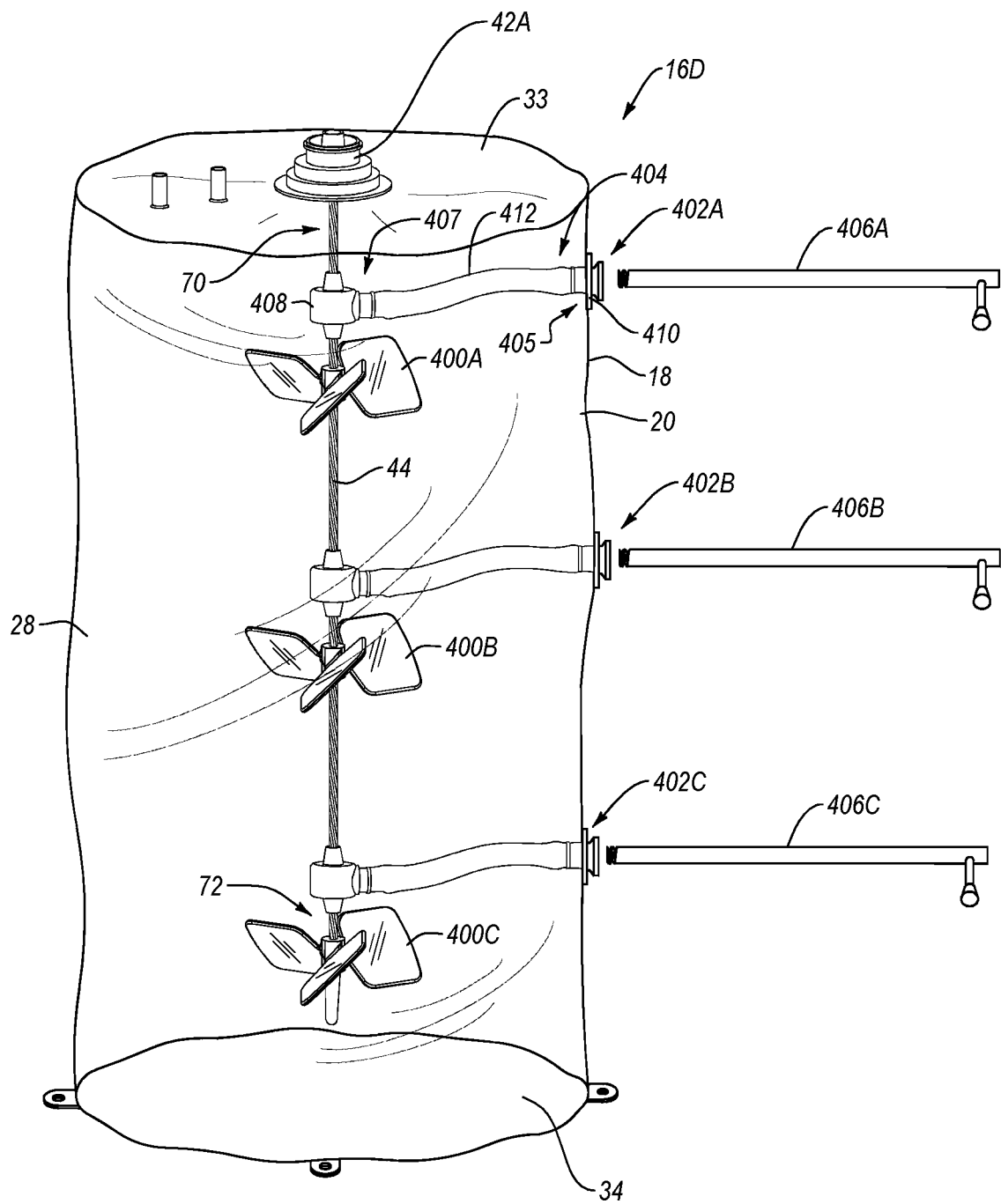
FIG. 23 is a partially exploded front view of the container assembly shown in FIG. 22.

As depicted in FIG. 23, container assembly 16A comprises container 18 having flexible drive line 44 disposed therein. First end 70 of flexible drive line 44 is secured to upper end wall 33 of container 18 by rotational assembly 42A. Mounted on flexible drive line 44 as spaced apart locations are mixing elements 400A-C. Each of mixing element 400A-C can comprise a fixed blade impeller, such as previously discussed impeller 46, a foldable impeller, such as previously discussed impellers 190, 225, 230, 238, or other types of mixing elements. In alternative embodiments, container assembly 16A can comprise one one, two, or four or more mixing elements 400. In contrast to container assembly 16 where second end 72 of drive line 44 is secured to lower end wall 34, container assembly 16A has second end 72 of drive line 44 suspended above lower end wall 34.

To stabilize drive line 44 within compartment 28 of container 18, container assembly 16A comprises lateral support assemblies 402A-C coupled with flexible drive line 44 at space apart locations along the length thereof. Each lateral support assembly 402A-C comprises a retention assembly 404 having a first end 405 secured to side 20 of container 18 and an opposing second end 407 secured to flexible drive line 44. Lateral support assembly 402 also includes a support rod 406 that is selectively received and secured within corresponding retention assembly 404. Each retention assembly 404 comprises a port fitting 410 at first end 405 that is coupled with side 20 of container 18, a receiver 408 at second end 407 that is mounted to flexible drive line 44, and a flexible tube 412 that extends between port fitting 410 and receiver 408.

Figure 24:
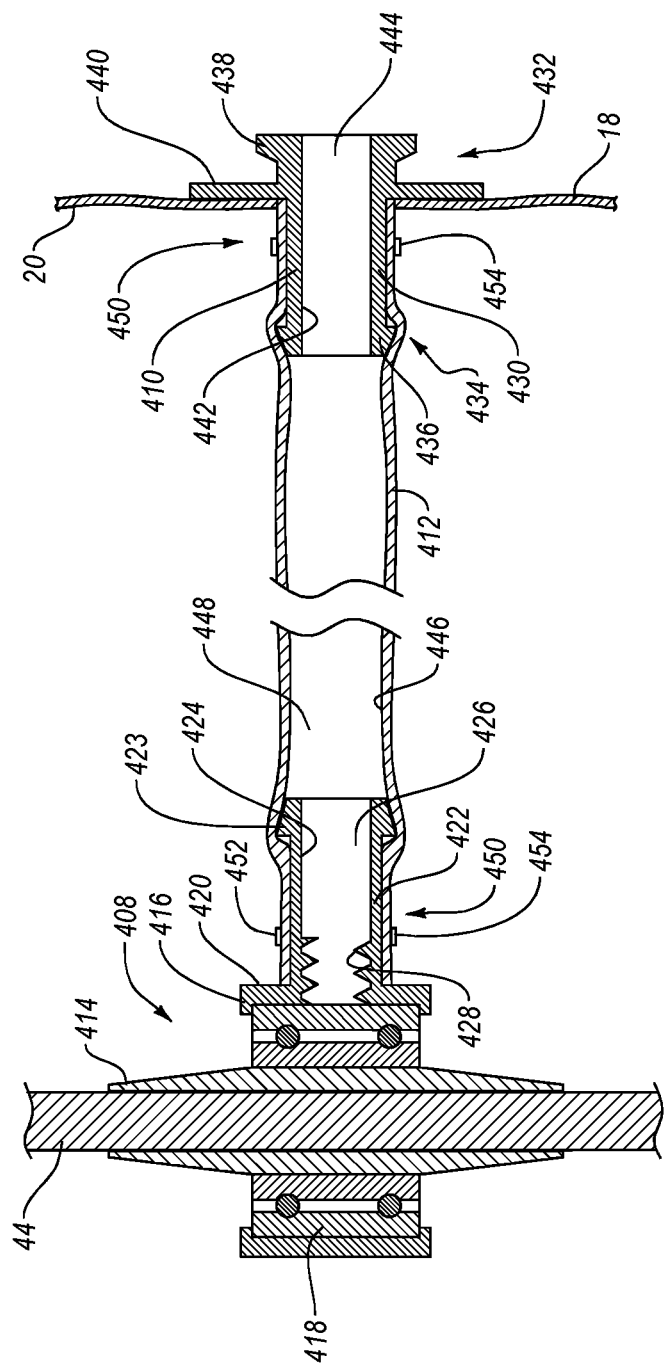
FIG. 24 is a cross sectional side view of a retention assembly which forms a portion of the lateral support assembly shown in FIG. 22.

As depicted in FIG. 24, receiver 408 comprises an inner housing 414 that is securely fixed to flexible drive line 44 such as by crimping, adhesive, clamps, fasteners, or the like. Receiver 408 also includes an outer housing 416 that encircles inner housing 414. A bearing 418, such as a ball thrust bearing, roller thrust bearing, or other type of bearing, is disposed between inner housing 414 and outer housing 416. Bearing 418 enables inner housing 414 and drive line 44 to rotate concurrently relative to outer housing 416. Outer housing 416 includes a body 420 having a tubular stem 422 outwardly projecting therefrom. Stem 422 can be integrally formed with or secured to body 420. An annular barb 423 can encircle and outwardly project on the end of stem 422 for engaging with flexible tube 412. Stem 422 has an interior surface 424 that bounds an opening 426 that can extend into body 420. Formed on interior surface 424 of stem 422 and/or body 420 is an engaging thread 428.

As also depicted in FIG. 24, port fitting 410 comprises a tubular stem 430 having a first end 432 and an opposing second end 434. An annular barb 436 can encircle and outwardly extending from second end 434 for engaging with flexible tube 412. Radially outwardly projecting from first end 432 is a retention flange 438. As will be discussed below in greater detail, retention flange 438 is used to secure port fitting 410 to rigid support housing 100. Retention flange 438 need not encircle stem 430 and can have a variety of different configurations. Encircling and radially outwardly projecting from stem 430 at a location between opposing ends 432 and 434 is a mounting flange 440. Mounting flange 440 is welded or otherwise secured to side 20 of container 18 so as to form a liquid tight seal therewith. As a result, first end 432 of port fitting 410 disposed outside of container 18 while second end 434 is disposed within container 18. Stem 430 has an interior surface 442 that bounds a passageway 444 extending therethrough.

Flexible tube 412 can comprise any type of flexible tube, tubing, hose, pipe or the like and is typically comprised of an elastomeric polymer. By making tube 412 flexible, tube 412 can be folded or rolled when collapsing container 18 for shipping, storage, disposal or the like. In an alternative embodiment it is appreciated that tube 412 need not be flexible but can be rigid or semi-rigid. Tube 412 has an interior surface 446 that bounds a passageway 448 that longitudinally extends through tube 412 from a first end 450 to an opposing second end 452. First end 450 of tube 412 is advanced over stem 430 of port fitting 410 so as to form a liquid tight seal therewith while second end 452 of tube 412 is received over stem 422 of receiver 408 so as to form a liquid tight seal therewith. A fastener 454 such as a pull tie, crimp, clamp, or similar structure can be secured around first end 450 and second end 452 so as to secure the engagement between tube 412 and stems 422 and 430.

Figure 25:
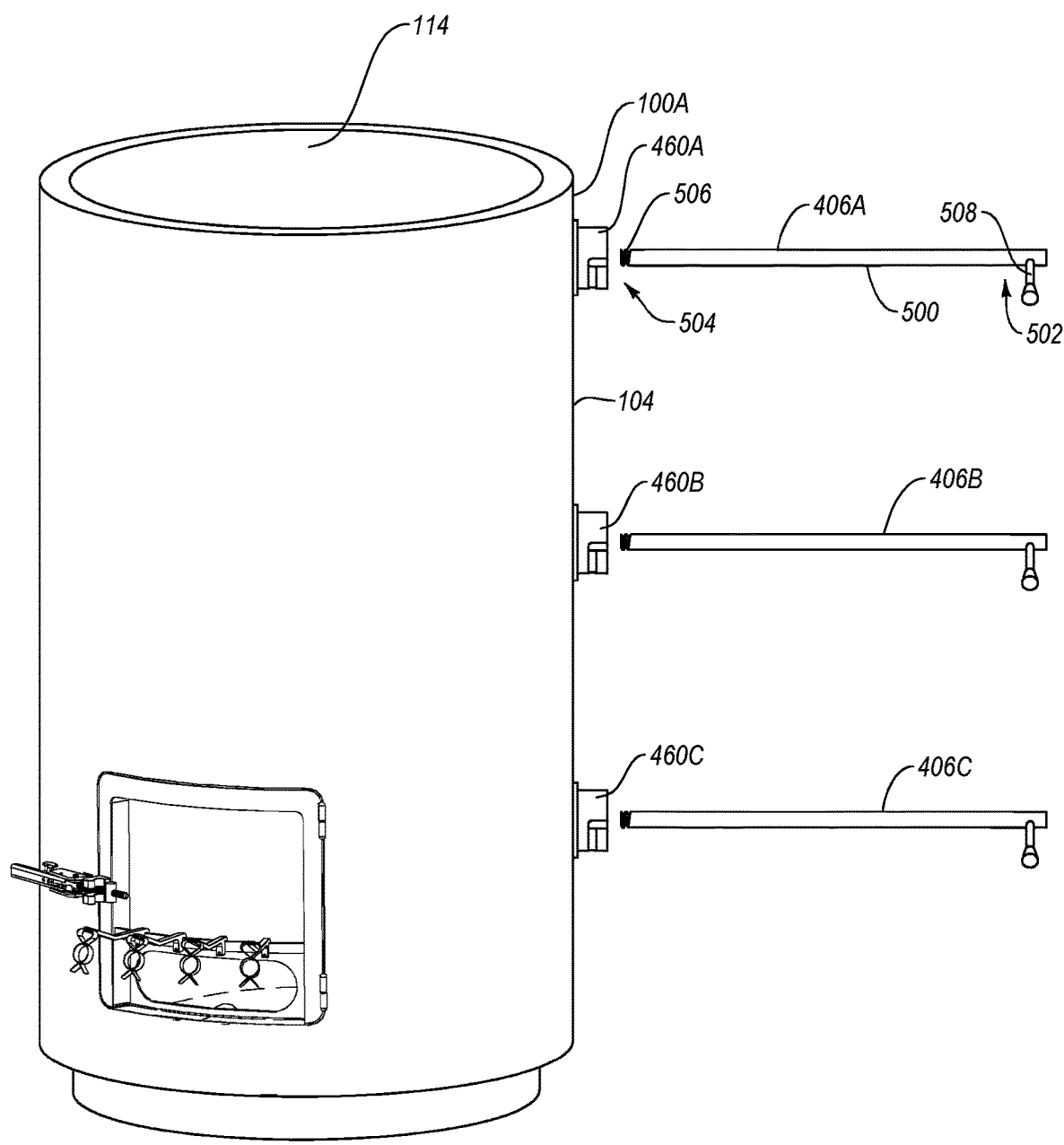
FIG. 25 is a perspective view of the support housing shown in FIG. 22 with support rods exploded therefrom.
Figure 26:
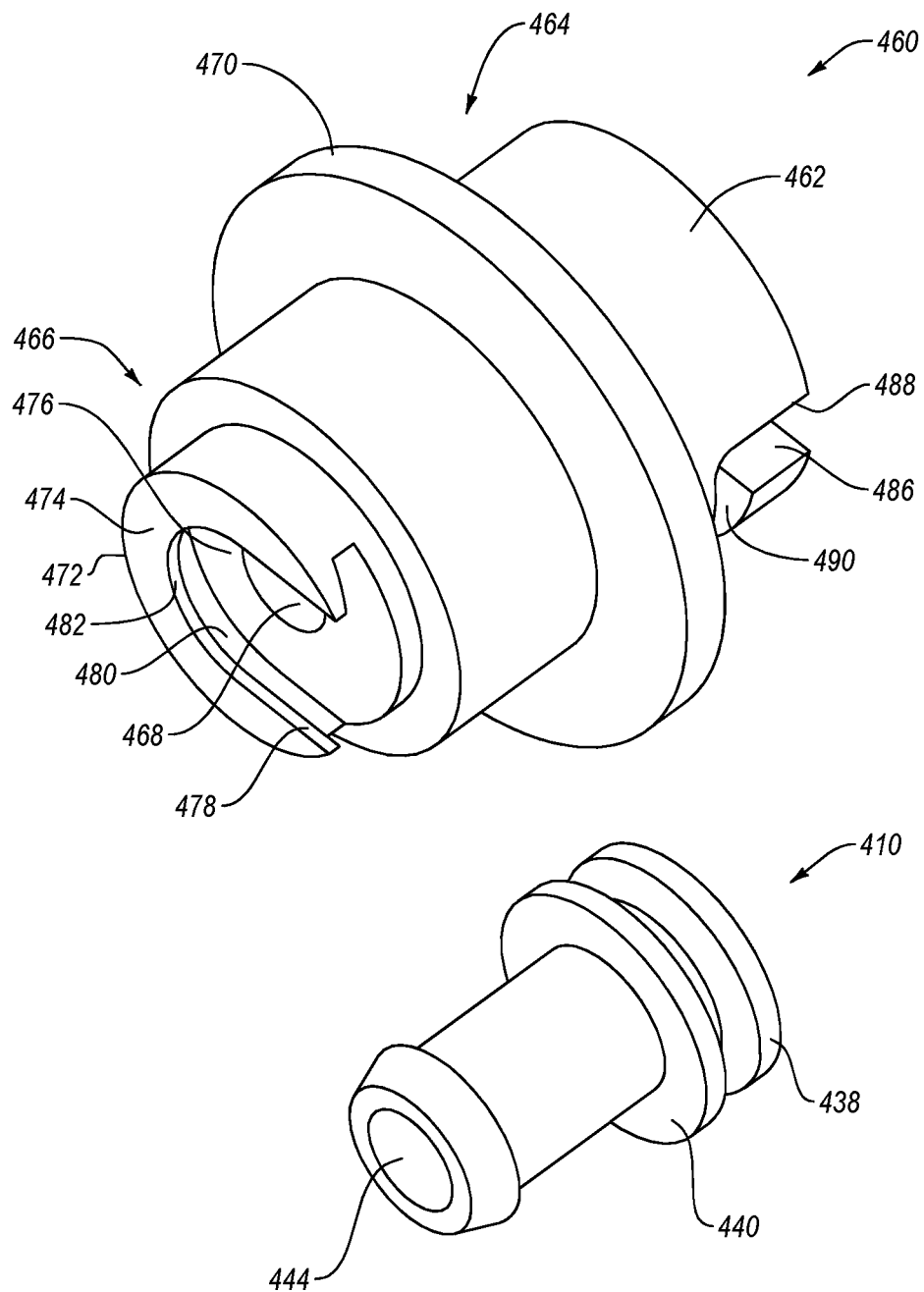
FIG. 26 is a perspective view of a locking insert that is disposed on the side of the support housing shown in FIG. 25.

During use, as depicted in FIG. 22, container assembly 16D is received within chamber 114 of support housing 100A. Support housing 100A is substantially identical is support housing 100 as previously discussed with regard to FIG. 1 and like elements are identified by like reference characters. Support housing 100A is distinguished from support housing 100 in that it does not include yoke 140 located on floor 110 (FIG. 1). Rather, support housing 100A includes a plurality of locking fittings 460A-C mounted at spaced apart locations on sidewall 104. As depicted in FIGS. 25 and 26, each locking fitting 460 comprises a base 462 having a first end 464 and an opposing second end 466. A passageway 468 centrally passes through base 462 between opposing ends 464 and 466. A flange 470 can encircle and radially outwardly project from base 462 at a location between opposing ends 464 and 466. During the manufacture of support housing 100A, vertically spaced apart holes 475 (FIG. 22) can be formed through sidewall 104 so as to extend to chamber 114. Second end 466 of each locking fitting 460 is received within a corresponding hole 475 so that flange 470 hits against the exterior surface of sidewall 104. Welding or other fastening techniques can then be used to secure each locking fitting 460 to support housing 100A within the corresponding hole 475.

Formed on the end face of base 462 at second end 466 is a catch 472. Catch 472 is disposed adjacent to interior surface 112 of support housing 100A and has a U-shaped body 474 with a U-shaped opening 476 passing therethrough. U-shaped opening 476 is aligned with passageway 468 passing through base 462. Body 474 has an interior surface 478 that includes an undercut U-shaped channel 480 and a U-shaped catch lip 482 that radially inwardly projects adjacent to channel 480. Catch 472 is configured so that retention flange 438 on port fitting 410 can be slidably received and captured within channel 480 so that passageway 468 of locking fitting 460 is aligned with passageway 444 of a corresponding port fitting 410. It is appreciated that retention flange 438 and/or channel 480 can be tapered so that a releasable friction fit is formed therebetween. It is also appreciated that there are a variety of different fastening techniques that can be used to releasably secure port fitting 410 to locking fitting 460.

Locking fitting 460 also includes a locking slot 486 formed on first end 464 of base 462 and which is located outside of support housing 100A. Locking slot 486 includes a first leg 488 that passes through base 462 to passageway 468 and runs parallel to passageway 468. Locking slot 486 also includes a second leg 490 that extends normal to first leg 488 at the end thereof so as to extend around a portion of the perimeter of base 462. Second leg 490 also extends to passageway 468.

Returning to FIG. 25, each support rod 406 comprises a linear shaft 500 that extends between a first end 502 and an opposing second end 504. A locking thread 506 is formed on second end 504. A locking arm 508 radially outwardly projects from shaft 500 as first end 502. Locking arm 508 is sized to be received within locking slot 486. Support rod 406 is typically comprised of metal but other rigid or semi-rigid materials can also be used.

Figure 27A:
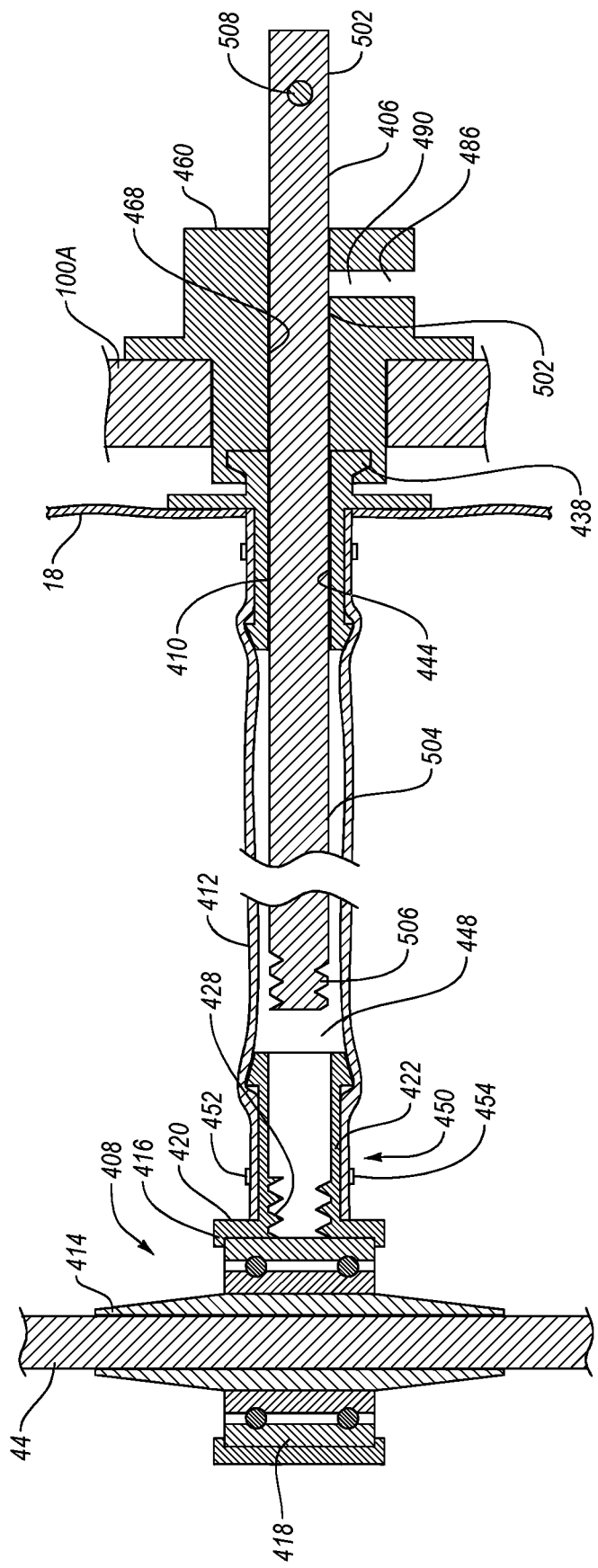
FIG. 27A is a cross sectional side view of the retention assembly having the support rod partially inserted therein.
Figure 27B:
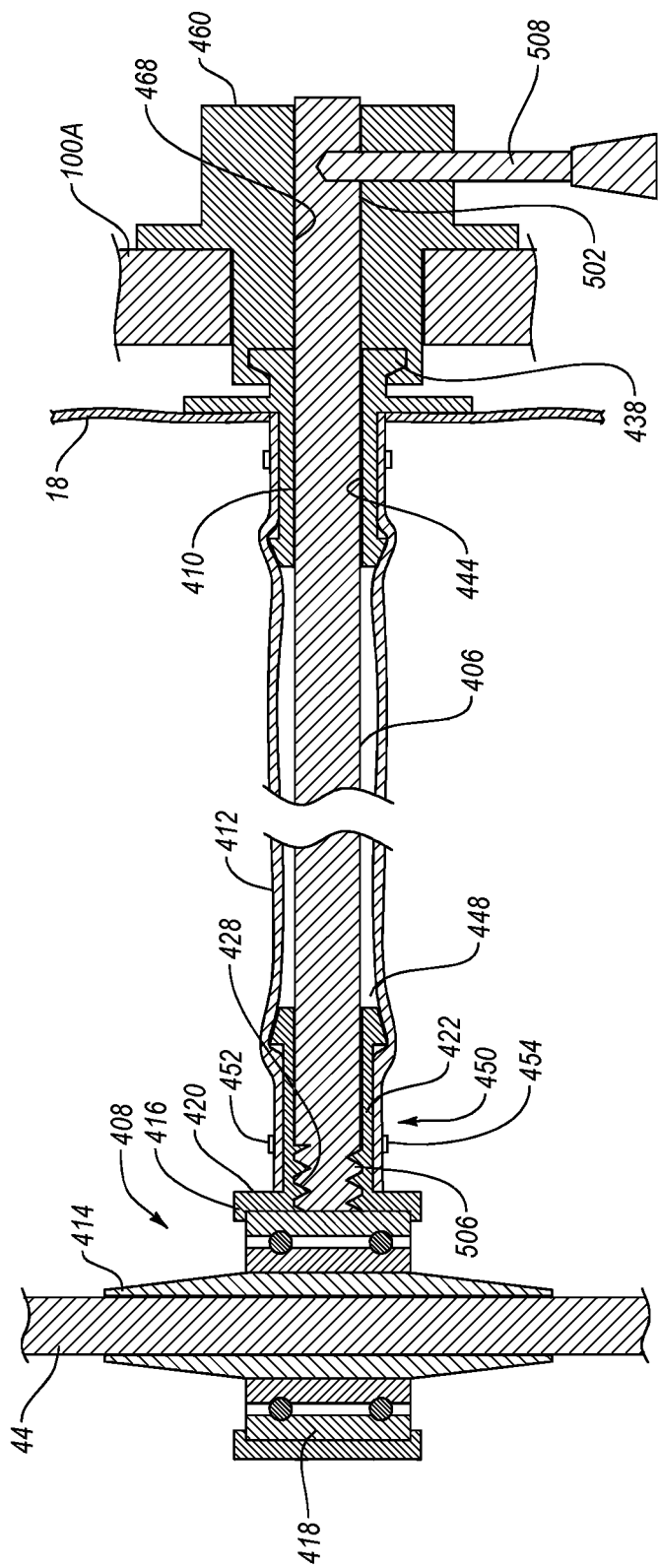
FIG. 27B is a cross sectional side view of the retention assembly having the support rod fully inserted and locked therein.

During use, as previously discussed and depicted in FIG. 22, container assembly 16D is received within chamber 114 of support housing 100A. Once inserted, each port fitting 410 is secured to a corresponding locking fitting 460 as previously discussed and depicted in FIG. 27A. In this assembled configuration, second end 504 of each support rod 406 is advanced through passageway 468 of locking fitting 460 through passageway 444 of port fitting 410 and into passageway 448 of tube 412. Each support rod 406 is continued to be advanced until locking thread 506 reach engaging thread 428 on retention assembly 404. Concurrently, locking arm 508 is received within first leg 488 (FIG. 26) of locking slot 486. In this position, locking arm 508 can be rotated downward through second leg 490 of locking slot 406 so as to lock support rod 406 to locking fitting 460. As locking arm 508 is rotated, shaft 500 with locking threads 506 thereon are rotated. As locking threads 506 are rotated they threadedly engage with engaging threads 428 on receiver 408, thereby securing support rod 406 to receiver 408. As a result, opposing ends of support rod 406 are secured to locking fitting 460 and receiver 408 which creates a lateral rigid support for flexible drive line 44. It is appreciated that a variety of other connections can be used for securing one or both of opposing ends of support rod 404 such as a bayonet connection, luer-lock connection, clamp, separate fastener, or the like.

The lateral rigid support of flexible drive line 44 achieves a number of benefits. For example, where mixing element 400 is an impeller, the rotation of the impeller causes the impeller to tend to migrate laterally. Lateral movement of drive line 44 and mixing elements 400 can cause damage to container 18 and can produce irregular mixing within container 14. Irregular mixing can be especially problematic where the mixing system is being used as a bioreactor or fermetor used for growing cells or microorganisms. In those cases, irregular mixing can apply unwanted shear forces on the cells or microorganisms or can result in irregular feeding or gas transfer to the cells or microorganisms. Use of the lateral support assemblies prevents unwanted lateral movement of drive line 44 and mixing elements 400 within container 18 and helps maintain uniform mixing. Although in the depicted embodiment three separate lateral support assemblies 402 are shown, in alternative embodiments, container assembly 16D can be formed with only one or two lateral support assemblies. Alternatively, four or more lateral support assemblies can also be used based on the size or other operational conditions for container assembly 16D.

Furthermore, as a result of the lateral support to drive line 44, second end 72 of drive line 44 need not be connected to lower end wall 34 of container 18. In some cases this is beneficial because it permits a more convenient folding of container 18. That is, in some designs for container 18, the most compact folding of container 18 requires that the center of opposing end walls 33 and 34 be pulled away from each other. Where drive line 44 is secured to the opposing end walls 33 and 34, the end walls cannot be pulled away from each other and thus container 18 cannot be folded in the most compact manner.

In addition, where the opposing ends of drive line 44 are connected to the top and bottom of container 18, as in FIG. 2, drive line 44 is tensioned to help prevent lateral walking of the impeller. As previously discussed, to facilitate the tension of drive line 44, the second end of container 18 is secured to the floor or relative to the floor of the support housing. In contrast, by using the lateral support assemblies, drive line 44 does not need to be tensioned and it is not necessary to secure the second end of container 18 to the floor of the support housing.

Figure 28:
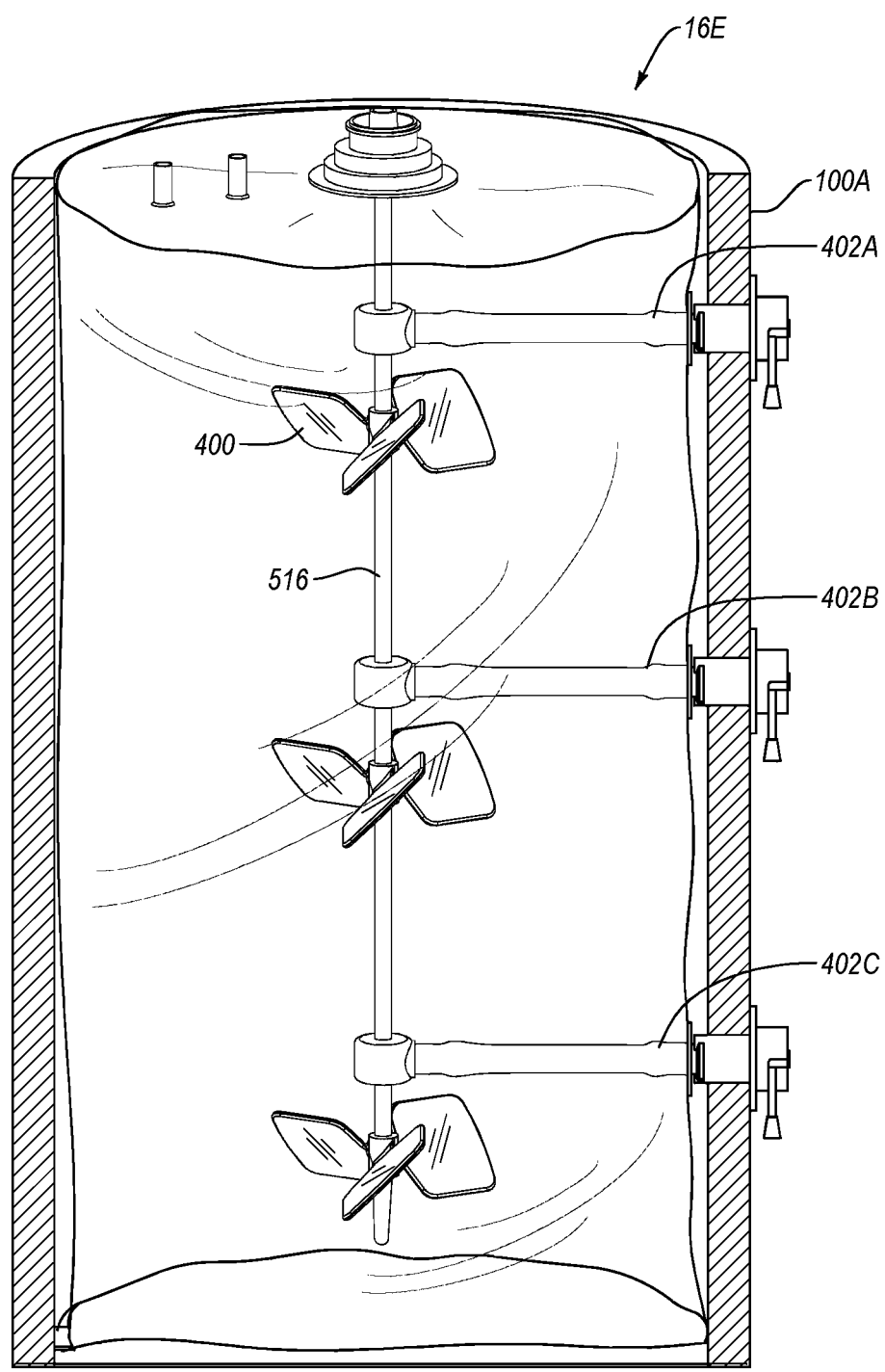
FIG. 28 is a cross sectional side view of a support housing having an alternative embodiment of a container assembly therein when the container assembly includes a rigid drive shaft.

Depicted in FIG. 28 is a container assembly 16E disposed within support housing 100A. Container assembly 16E includes lateral support assemblies 402A-C. However, in contrast to being connected to flexible drive line 44, container assembly 16E includes a rigid drive shaft 516 such as drive shaft 352 as depicted in FIG. 20. Lateral support assemblies 402 facilitate the lateral support of drive shaft 516 along the length thereof. Again, any number of lateral support assemblies 402 can be used and any number of mixing elements 400 can be mounted thereon. Other alternative embodiments as previously discussed with regard to like elements of container assembly 16D are also applicable container assembly 16D.

In another alternative embodiment, a container assembly can be formed that includes impeller assembly 40C as depicted and previously discussed with regard to FIG. 21. One or more lateral support assemblies 402 can extend between the side of container 18 and tubular connector 442. The container assembly can be housed within support housing 100A.

Figure 29:
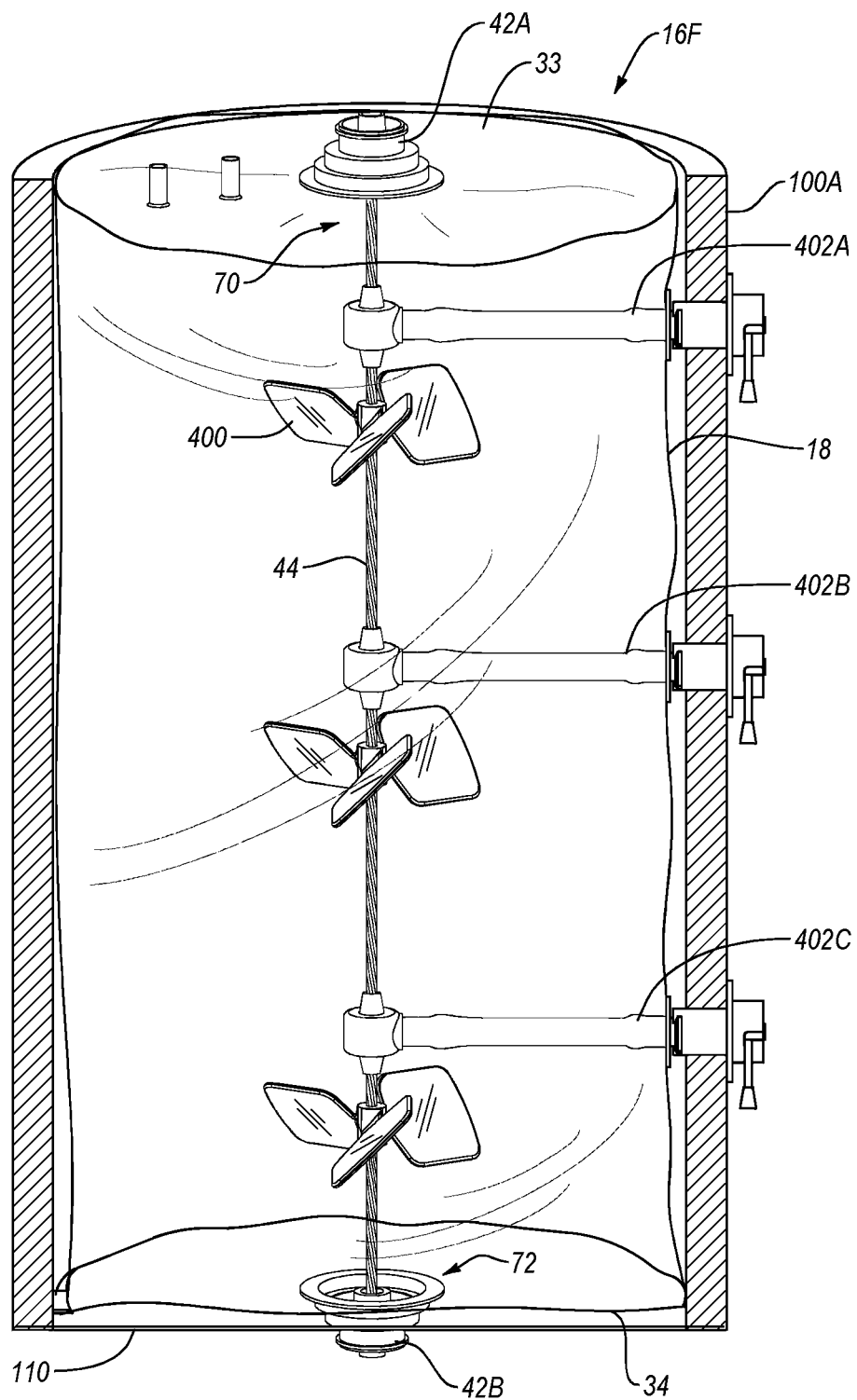
FIG. 29 is a cross sectional side view of a support housing having an alternative embodiment of a container assembly therein when the drive line is connected to both the upper end wall and the lower end wall and is supported by lateral support assemblies.

Depicted in FIG. 29 is another alternative embodiment of a container assembly 16F disposed within support housing 100A. Container assembly 16F is used where greater stability of drive line 44 is required, such as for long containers 18. Container assembly 16F comprises container 18 housing drive line 44 on which one or more mixing elements 400 are disposed. First end 70 of drive line 44 is secured to upper end wall 33 by first rotational assembly 42A and second end 72 of drive line 44 is secured to lower end wall 34 by second rotational assembly 42B in the same manner as previously discussed with regard to container assembly 16 depicted in FIGS. 2 and 3. In turn, second rotational assembly 42B can be secured to floor 110 of support housing 100A using one of the yokes previously discussed or can be otherwise secured in place. Container assembly 16F also includes one or more lateral support assemblies 402 extending between side 20 of container 18 and flexible drive line 44 as previously discussed with regard to container assembly 16D depicted in FIGS. 22-24. Thus, in this embodiment flexible drive line 44 is supported both at opposing ends and at one or more locations along its length. Use and alternative embodiments as discussed with the other container assemblies are also applicable to container assembly 16F.

Figure 30:
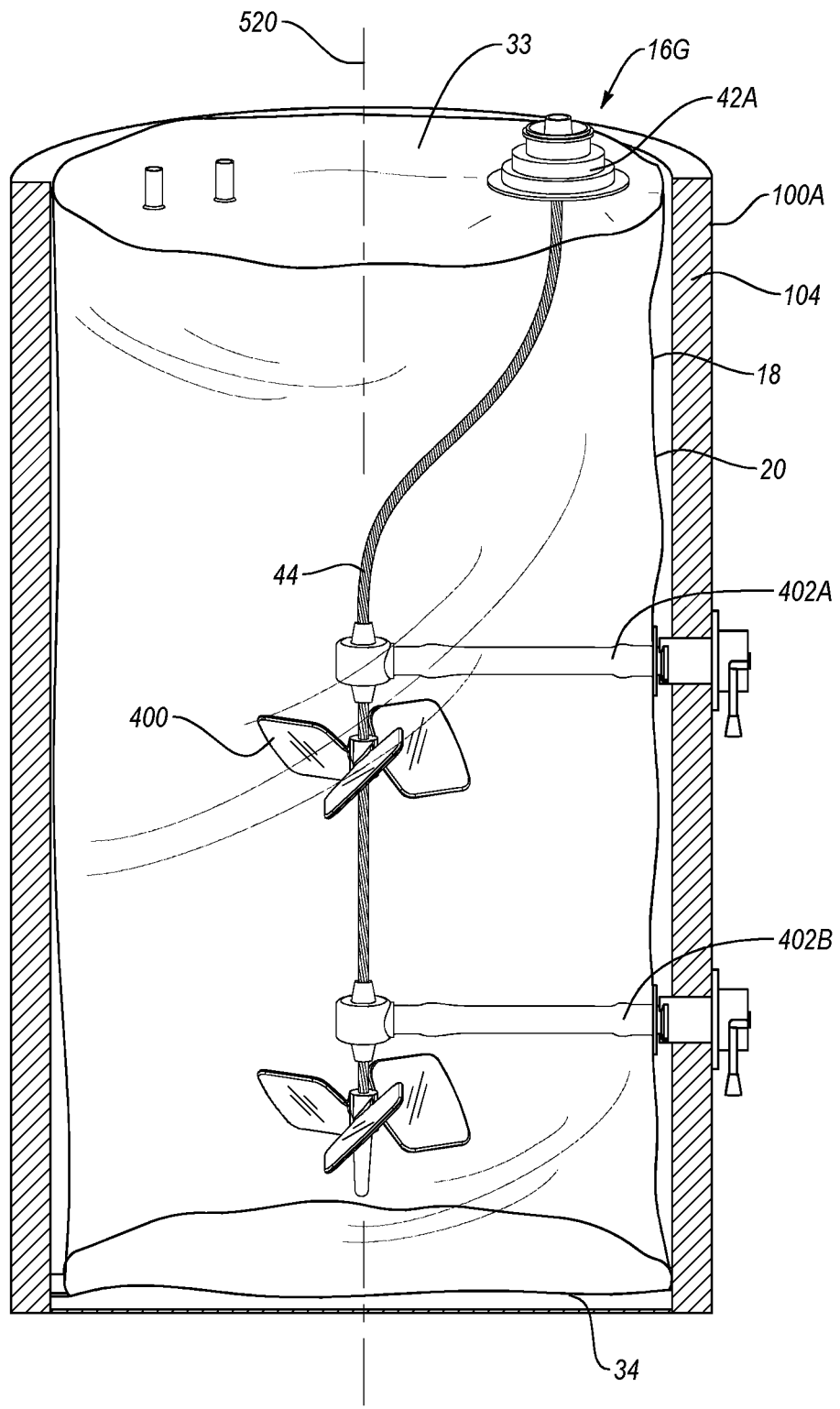
FIG. 30 is an elevated side view of the container assembly shown in FIG. 23 wherein the rotational assembly connected to the drive line has been moved closer to the sidewall of the support housing.

Finally, depicted in FIG. 30 is another alternative embodiment of a container assembly 16G disposed within support housing 100A. Container assembly 16G is substantially the same as container assembly 16D and thus the prior disclosure, alternative embodiments and reference characters for container assembly 16D are also applicable to container assembly 16E. Container 18 has a central longitudinal axis 520 that extends between upper end wall 33 and lower end wall 34. In container assembly 16D, rotational assembly 42A is mounted on upper end wall 33 in alignment with central longitudinal axis 520 and drive line 44 extends along central longitudinal axis 520. In contrast, container assembly 16G has rotational assembly 42A disposed on upper end wall 33 at a location spaced apart from central longitudinal axis 520 and, more specifically, adjacent to sidewall 104 of support housing 100A. However, lateral support assemblies 402 hold the portion of drive line 44 on which mixing elements 400 are disposed, along central longitudinal axis 520.

Container assembly 16G has the advantage that mixing elements 400 are still centrally disposed within container 18 so that the fluid within container 18 can have uniform mixing but the central area of upper end wall 33 is now openly exposed. As such, ports, fitting, probes, sample tubes and the like can now be centrally mounted on upper end wall 33, which is often considered a valuable location. Furthermore, placing rotational assembly 42A closer to sidewall 104 of support housing 100A can make it easier to connect rotational assembly 42A to drive motor assembly 300 (FIG. 1). Thus, because of the flexible nature of drive line 44 and the rigid lateral support produced by lateral support assemblies 402, rotational assembly 42A can be located at any position on upper end wall 33 and even at the upper end of side 20 of container 18.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A fluid mixing system comprising:
   a container bounding a compartment, the compartment being configured to hold a fluid;
   an elongated drive line or drive shaft at least partially disposed within the compartment of the container, the drive line or drive shaft being rotatable relative to the container; and
   a first impeller disposed within the compartment of the container, the first impeller comprising:
      a hub secured to the drive line or drive shaft, the hub having a central longitudinal axis extending therethrough;
      a flange radially outwardly projecting from the hub and projecting radially outwardly away from the central longitudinal axis of the hub, the flange comprising a stop projecting therefrom with a key projecting from the stop, wherein the stop has a greater width than the key; and
      a plurality of blades being pivotably coupled to the flange, each of the plurality of blades comprising:
         an elongated arm extending between a first end and an opposing second end, the elongated arm comprising an axle disposed at the first end of the elongated arm, wherein the first end is pivotably coupled to the flange by the axle so that the elongated arm pivots about a rotational axis, the rotational axis being disposed parallel to the central longitudinal axis of the hub; and
         an enlarged blade head disposed at the second end of the elongated arm.

2. The fluid mixing system as recited in claim 1, further comprising a retainer completely encircling the central longitudinal axis of the hub and being secured to the flange, the first end of the elongated arm of each of the plurality of blades being pivotably disposed within a slot bound between the flange and the retainer.

3. The fluid mixing system as recited in claim 1, wherein the plurality of blades are pivotable between a collapsed position and an expanded position, each of the plurality of blades having a terminal tip that is closer to the drive line or drive shaft when the blades are in the collapsed position than when in the expanded position.

4. The fluid mixing system as recited in claim 1, wherein the container comprises a collapsible bag made of one or more sheets of polymeric film.

5. The fluid mixing system as recited in claim 1, wherein the elongated drive line or drive shaft comprises the drive line, the drive line being at least partially disposed within the compartment of the container and having the hub secured thereto, the drive line having a length extending between a first end rotatable connected to a first end of the container and a second end rotatably connected to a second end of the container, at least 30% of the length of the drive line being sufficiently flexible that the at least 30% of the length can be twisted under torsion over an angle of at least 45° without plastic deformation.

6. The fluid mixing system as recited in claim 5, further comprising:
  a first rotational assembly including:
    a first casing mounted to a first end of the container; and
    a first hub rotatably mounted to the first casing, the first hub being coupled to a first end of the drive line; and
  a second rotational assembly including:
    a second casing mounted to a second end of the container; and
    a second hub rotatably mounted to the second casing, the second hub being coupled to a second end of the drive line.

7. The fluid mixing system as recited in claim 5, wherein the drive line is comprised of a flexible cable, cord, or tube.

8. The fluid mixing system as recited in claim 5, further comprising:
  a drive shaft,
  wherein the drive line comprises a tube, and
  wherein the drive shaft is removably positioned within the tube.

9. The fluid mixing system as recited in claim 1, further comprising:
  a dynamic seal sealing the drive shaft to the container,
  wherein the elongated drive line or drive shaft comprises the drive shaft, the drive shaft being at least partially disposed within the compartment of the container.

10. The fluid mixing system as recited in claim 1, further comprising a second impeller coupled to the drive line or drive shaft, the second impeller being spaced apart from the first impeller.

11. A fluid mixing system comprising:
  a container bounding a compartment, the container having a first end and an opposing second end and comprising a collapsible bag formed from one or more sheets of polymeric film;
  a drive line disposed within the compartment of the container, the drive line having a length extending between a first end and an opposing second end, the first end of the drive line being rotatably connected to the first end of the container and the opposing second end of the drive line being rotatably connected to the second end of the container, at least 30% of the length of the drive line being sufficiently flexible that the at least 30% of the length can be twisted under torsion over an angle of at least 45° without plastic deformation; and
  a first impeller disposed within the compartment of the container, the first impeller comprising:
  a hub secured to the drive line;
  a flange radially outwardly projecting from the hub, the flange comprising a stop projecting therefrom with a key projecting from the stop, wherein the stop has a greater width than the key; and
  a plurality of blades being pivotably coupled to the flange, each of the plurality of blades comprising:
  an elongated arm having a first end and an opposing second end, the elongated arm comprising an axle disposed at the first end of the elongated arm, wherein the first end is pivotably coupled to the flange by the axle; and
  an enlarged blade head disposed at the second end of the elongated arm.

12. The fluid mixing system as recited in claim 3, wherein the plurality of blades are mechanically stopped when moved to the collapsed position and the expanded position and wherein the entire blade head of each of the plurality of blades is disposed radially outward from the flange when the plurality of blades are in the collapsed position and the expanded position.

13. The fluid mixing system as recited in claim 3, wherein at least a portion of the second end of the elongated arm of each of the plurality of blades is disposed radially outward from the flange when the plurality of blades are in the collapsed position and the expanded position.

14. The fluid mixing system as recited in claim 1, wherein the enlarged blade head of each of the plurality of blades has a flat rectangular face.

15. The fluid mixing system as recited in claim 3, further comprising the flange having a first side face facing a first end of the container and an opposing second side face facing a second end of the container, wherein the stop outwardly projects from the first side face of the flange, the elongated arm of a select one of the plurality of blades butting against the stop when the select one of the plurality of blades is in the expanded position.

16. The fluid mixing system as recited in claim 2, wherein the key outwardly projects away from the flange and is received within a keyway formed on the retainer.

17. The fluid mixing system as recited in claim 1, wherein the enlarged blade head has an inside edge that intersects with the elongated arm, an opposing outside edge, and opposing top and bottom edges that extend between the inside edge and the outside edge, wherein at least a portion of the inside edge is freely and openly exposed.

18. The fluid mixing system as recited in claim 1, wherein for each of the plurality of blades, the elongated arm can be pivoted to a position so that the enlarged blade head is spaced apart from the flange.

19. The fluid mixing system as recited in claim 1, wherein for each of the plurality of blades, the enlarged blade head outwardly projects along a portion of a length of the elongated arm, the length extending between the first end and the opposing second end of the elongated arm.

20. The fluid mixing system as recited in claim 1, wherein for each of the plurality of blades, the enlarged blade head outwardly projects from opposing sides of the elongated arm.

21. The fluid mixing system as recited in claim 1, wherein for each of the plurality of blades, the enlarged blade head outwardly projects from the elongated arm so that an inside angle is formed therebetween.

22. A fluid mixing system comprising:
  a container bounding a compartment, the compartment being configured to hold a fluid;
  an elongated drive line or drive shaft at least partially disposed within the compartment of the container, the drive line or drive shaft being rotatable relative to the container; and
  a first impeller disposed within the compartment of the container, the first impeller comprising:
  a hub secured to the drive line or drive shaft, the hub having a central longitudinal axis extending therethrough;

a flange radially outwardly projecting from the hub and projecting radially outwardly away from the central longitudinal axis of the hub, the flange comprising a stop projecting therefrom with a key projecting from the stop, wherein the stop has a greater width than the key;

a retainer at least partially encircling the hub, the retainer being spaced apart from the flange along the central longitudinal axis of the hub so that a slot is formed between the retainer and the flange; and a plurality of blades being pivotably coupled to the flange, each of the plurality of blades comprising:

an elongated arm extending between a first end and an opposing second end, the elongated arm comprising an axle disposed at the first end of the elongated arm, wherein the first end is pivotably coupled to the flange by the axle with the axle of the first end being disposed within the slot between the retainer and the flange; and an enlarged blade head disposed at the second end of the elongated arm.

23. The fluid mixing system as recited in claim 22, wherein the flange and the retainer both completely encircle the hub.

24. The fluid mixing system as recited in claim 1, wherein the stop has a greater width than the key in a direction perpendicular to the central longitudinal axis of the hub.

25. The fluid mixing system as recited in claim 11, wherein the hub has a central longitudinal axis extending therethrough and the stop has a greater width than the key in a direction perpendicular to the central longitudinal axis of the hub.

26. The fluid mixing system as recited in claim 22, wherein the stop has a greater width than the key in a direction perpendicular to the central longitudinal axis of the hub.

* * * * *